US011540935B2

(12) United States Patent
Grim et al.

(10) Patent No.: US 11,540,935 B2
(45) Date of Patent: Jan. 3, 2023

(54) WELDED BACK BRACE

(71) Applicant: Ortho Systems, Agoura Hills, CA (US)

(72) Inventors: Tracy E. Grim, Thousand Oaks, CA (US); Kenji Watabe, Ventura, CA (US); Edwin Erwin, Studio City, CA (US)

(73) Assignee: Ortho Systems, Agoura Hills, CA (US)

( * ) Notice: Subject to any disclaimer, the term of this patent is extended or adjusted under 35 U.S.C. 154(b) by 626 days.

(21) Appl. No.: 15/616,860

(22) Filed: Jun. 7, 2017

(65) Prior Publication Data
US 2018/0353314 A1 Dec. 13, 2018

(51) Int. Cl.
*A61F 5/02* (2006.01)

(52) U.S. Cl.
CPC .................................. *A61F 5/028* (2013.01)

(58) Field of Classification Search
CPC .. A61F 5/02; A61F 5/022; A61F 5/024; A61F 5/026; A61F 5/028; A61F 5/03; A61F 5/50; A61F 5/0193; A61F 5/01; A61F 5/0102; A61F 5/0104; A61F 5/24; A61F 5/26; A61F 5/30; A61F 5/32; A61F 5/34; A61F 5/05; A61F 5/3738; A61F 5/0123; A61H 1/008; A61H 1/006; A61H 2201/1623; A61H 2201/1626; A42B 3/127; A61L 15/12
See application file for complete search history.

(56) References Cited

U.S. PATENT DOCUMENTS

| 4,572,167 | A | * | 2/1986 | Brunswick | A61F 5/028 2/44 |
| 4,624,248 | A | * | 11/1986 | Poole et al. | A61F 5/34 128/DIG. 20 |
| 5,178,163 | A | * | 1/1993 | Yewer, Jr. | A41F 9/002 128/876 |
| 5,628,721 | A | * | 5/1997 | Arnold | A61F 5/028 128/118.1 |
| 2001/0008955 | A1 | * | 7/2001 | Garth | A61F 5/028 602/19 |
| 2004/0077981 | A1 | * | 4/2004 | Weaver, II | A61F 5/028 602/19 |
| 2004/0193082 | A1 | * | 9/2004 | Cofre | A61F 5/3738 602/19 |

(Continued)

FOREIGN PATENT DOCUMENTS

GB 2544291 A * 5/2017 ............... A61F 5/03

OTHER PUBLICATIONS

"Calenders and Calendering Equipment Information". Global Spec. Engineering 360. https://www.globalspec.com/learnmore/manufacturing_process_equipment/web_handling_processing_equipment/calenders_calendering_equipment (Year: 2019).*

(Continued)

*Primary Examiner* — Ophelia A Hawthorne
*Assistant Examiner* — Gina McCarthy
(74) *Attorney, Agent, or Firm* — Fulwider Patton LLP

(57) ABSTRACT

A welded orthopedic back brace is disclosed. In an embodiment, at least one belt member is coupled to a spinal support element. The materials of the belt member are thermally fused to form a unitary segment. In another embodiment, an anterior portion of a posterior pad of the spinal support element includes thermally fused materials to provide a user with an added degree of comfort.

11 Claims, 21 Drawing Sheets

(56) References Cited

U.S. PATENT DOCUMENTS

| | | | | |
|---|---|---|---|---|
| 2006/0287625 | A1* | 12/2006 | Rauch | A61F 5/024 |
| | | | | 602/18 |
| 2007/0232973 | A1* | 10/2007 | Serola | A61F 5/0193 |
| | | | | 602/19 |
| 2008/0171955 | A1* | 7/2008 | Jaccard | A61F 5/028 |
| | | | | 602/19 |
| 2010/0217167 | A1* | 8/2010 | Ingimundarson | A61F 5/028 |
| | | | | 602/19 |
| 2011/0004135 | A1* | 1/2011 | Kausek | A61F 5/0123 |
| | | | | 602/16 |
| 2011/0295169 | A1* | 12/2011 | Hendricks | A61F 5/028 |
| | | | | 602/19 |
| 2013/0237891 | A1* | 9/2013 | Fryman | A61F 5/028 |
| | | | | 602/19 |
| 2014/0135672 | A1* | 5/2014 | Joseph | A61F 5/028 |
| | | | | 602/19 |
| 2014/0303536 | A1* | 10/2014 | Guldalian | A61F 5/028 |
| | | | | 602/19 |
| 2015/0148727 | A1* | 5/2015 | Collier | A61F 5/03 |
| | | | | 602/19 |
| 2018/0065027 | A1* | 3/2018 | Warmouth | A42B 3/127 |
| 2019/0314542 | A1* | 10/2019 | Ish Cassit | A61L 15/12 |

OTHER PUBLICATIONS

"Flame Lamination" Quality Composites, Inc., http://www.flamebonding.com/flame-lamination/ (Year: 2019).*

* cited by examiner

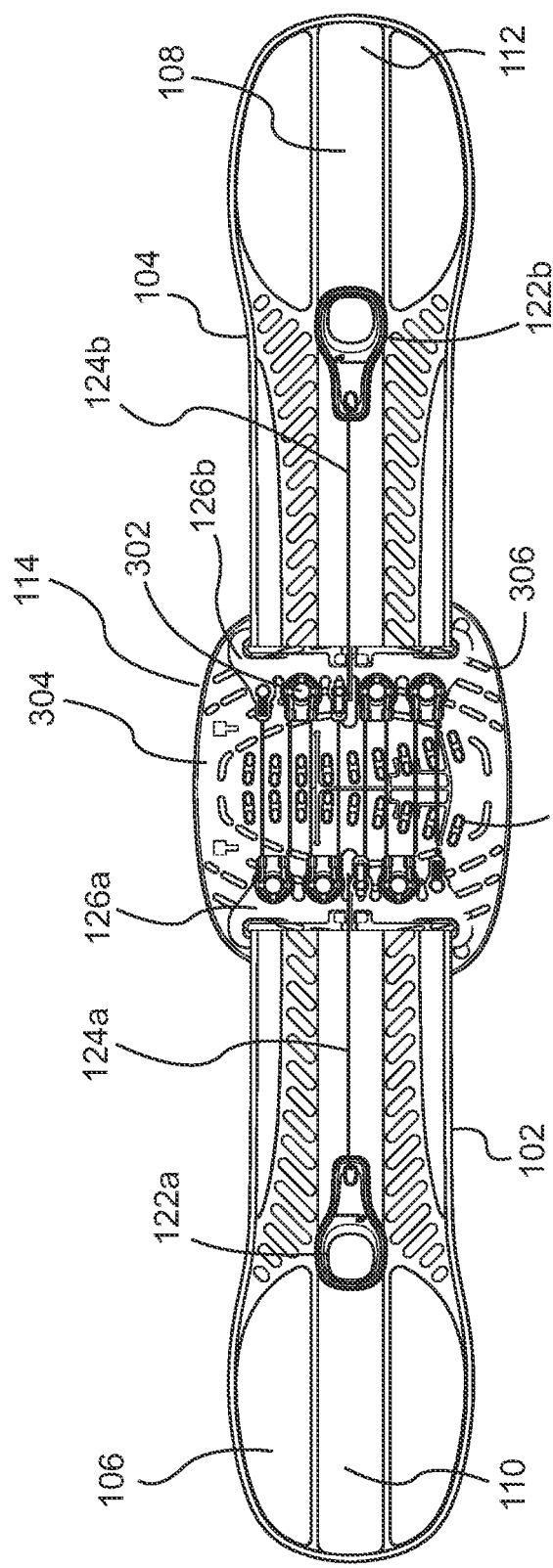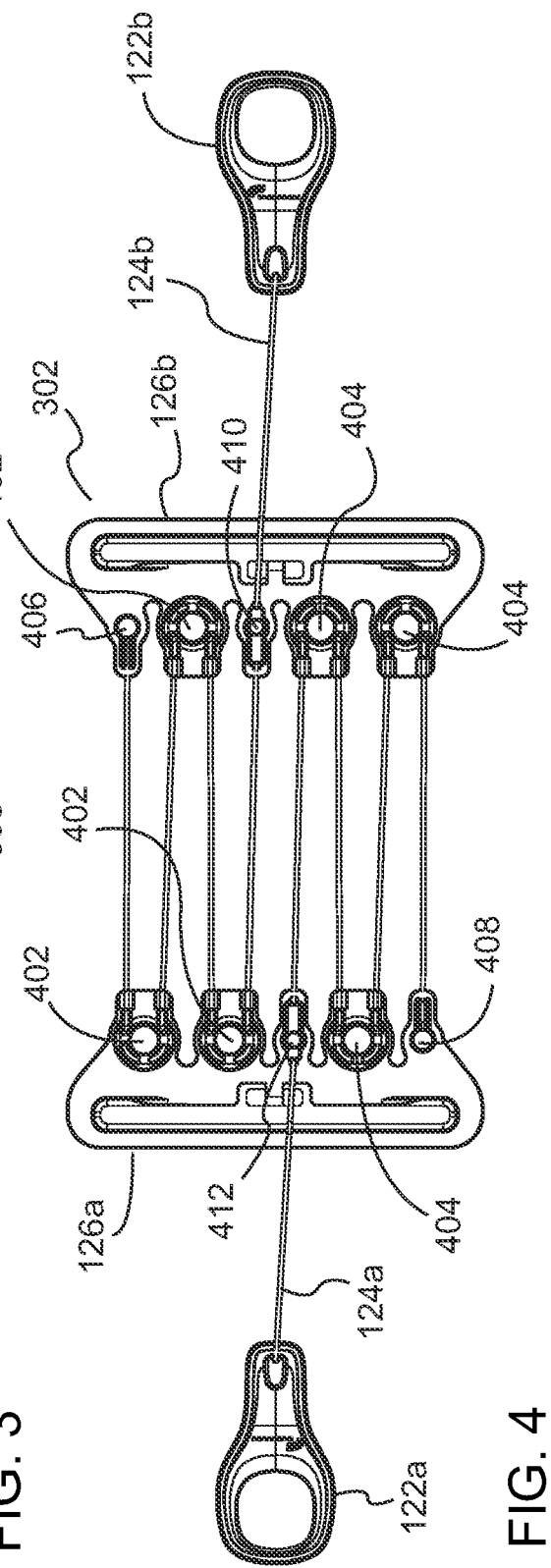
FIG. 3
FIG. 4

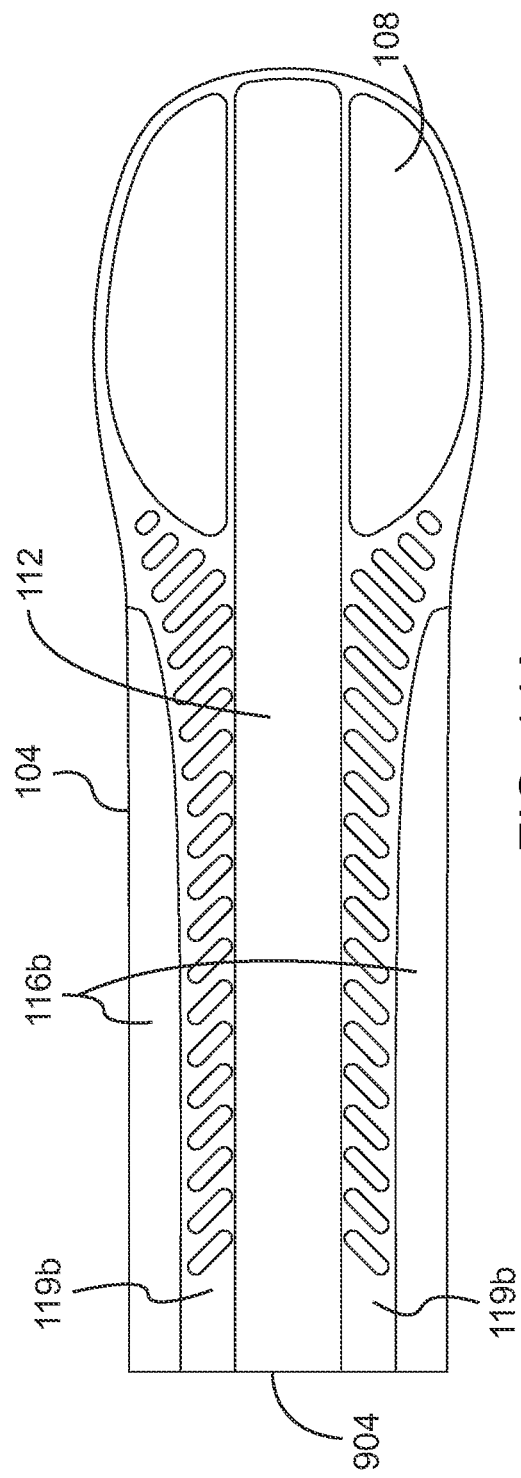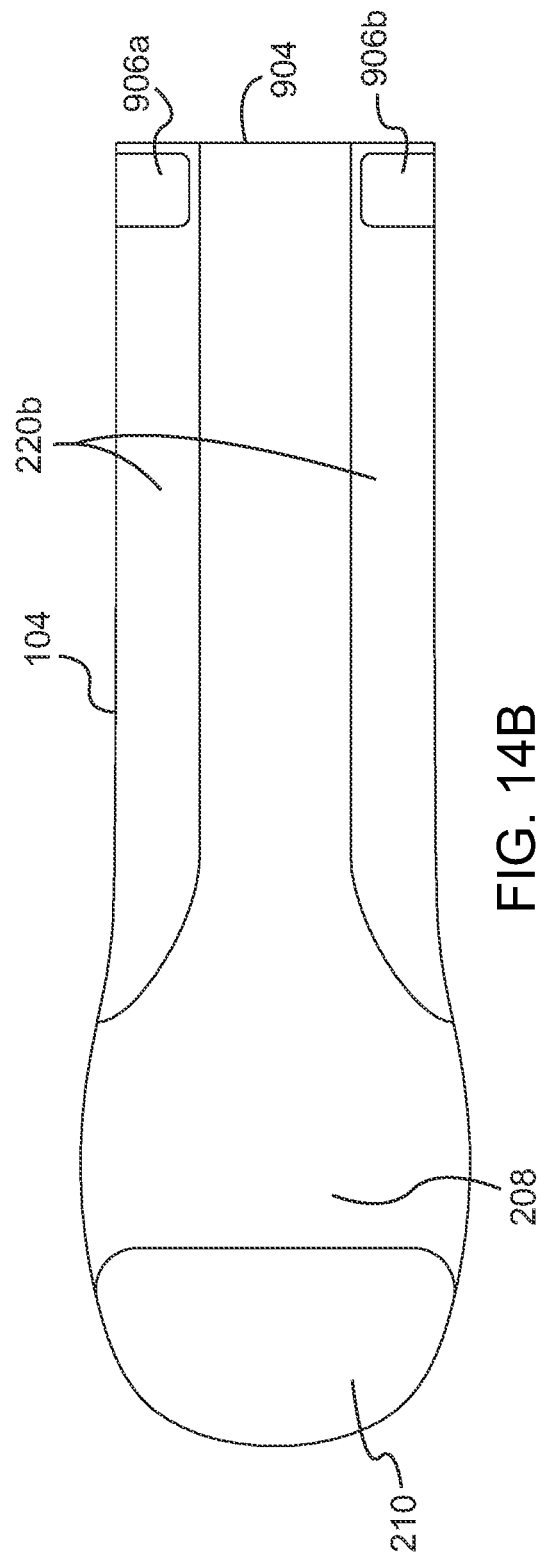
FIG. 14A
FIG. 14B

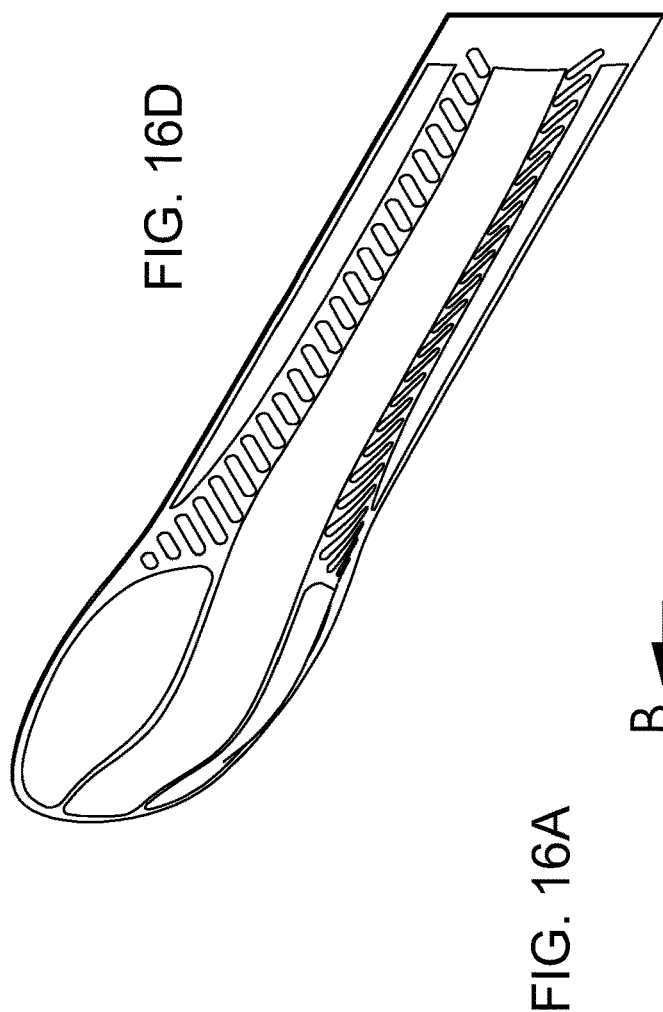
FIG. 16A
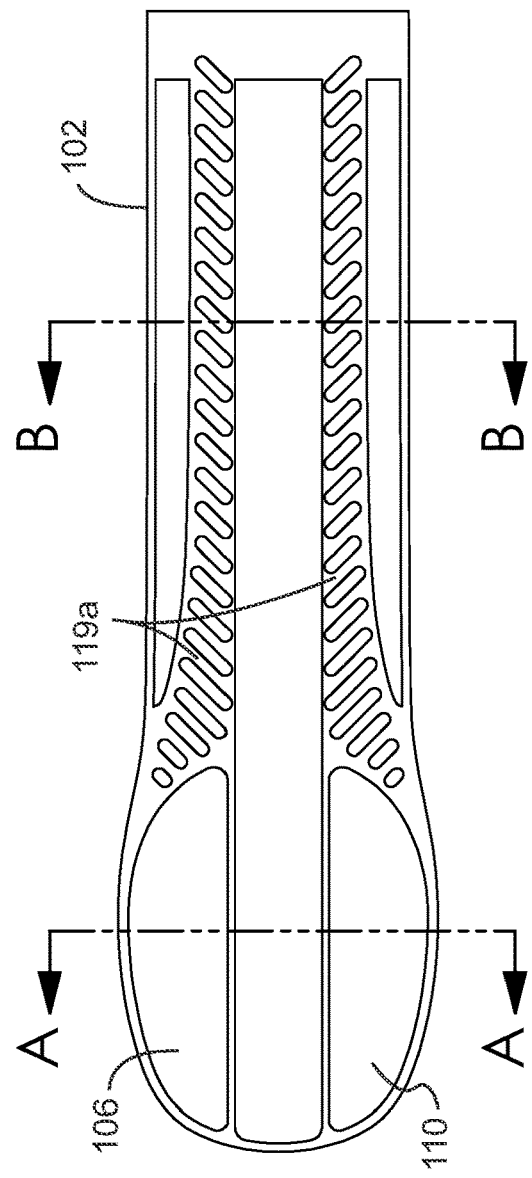
FIG. 16D
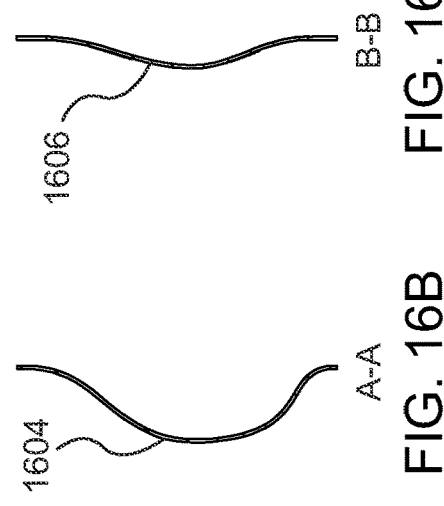
FIG. 16B
FIG. 16C

WELDED BACK BRACE

BACKGROUND

Field

The present disclosure relate generally to anatomical supports, and more particularly, to a compact orthopedic back brace having materials welded using thermal fusion.

Background

A number of orthopedic back braces are commercially available for individuals suffering from various categories of back pain. Such back braces are configured to serve a number of purposes depending on the application to the individual. Generally, orthopedic back braces can assist in providing proper alignment of the spine. Incorrect spinal alignment can cause chronic pain, weakness and other progressive conditions. Orthopedic back braces typically include a posterior spinal element for placement against a user's back, and a belt assembly having one or more belt straps for securing the posterior spinal element to the user's back. The belt assembly may assist in enabling the posterior spinal element to press against the relevant area of the user's spine to thereby straighten the spine and relieve discomfort.

Conventional back braces have deficiencies. For example, many or most such orthopedic back braces typically have elements that are sewn together or otherwise held together using stiches or similar means. Such elements include, among others, the belt straps, which often have several layers that are stitched together at one or more borders in order to provide a specific amount of rigidity and elasticity to enable the belt to perform its functions properly. The spinal element typically also involves a collection of materials stitched or sewn together.

Because of the stitching, the internal layers of the belt (or spinal element) typically are independent of, and can often move relative to, one another. As a result, the separating belt elements can make the belt assembly more voluminous than necessary and undesirable for a wearer. For example, the independently acting layers of the belt member can spread in some areas and bunch up in other areas due to shear forces. The result is a generally unwieldy and bulky fit. Moreover, because each such layer can effective act independently as described above, the desired properties of the belt (e.g., rigidity, stiffness, elasticity) for achieving a given orthopedic or medical objective often cannot be well controlled.

Another problem with such conventional back braces is that the physical properties and characteristics of the belt typically lack spatial continuity. That is, because layers of different materials often simply overlap without otherwise being connected except at predefined seams, the properties of the materials (such as the rigidity, flexibility, etc.) can change rapidly at seam borders. More specifically, in areas on the belt adjacent sewn borders, such belts typically have abrupt discontinuities in its various properties because different materials (or identical materials with different thicknesses) are directly sewn together at the predefined borders. Thus, the belt may provide a region of one or more generally elastic materials that are connected, at a sewn border, to a rigid, inelastic material. The user can usually feel these abrupt discontinuities and the attendant discomfort that can result, particularly when the belt is worn for a long time.

Other conventional solutions for the belt assembly have included combining a plurality of layers using lamination or an adhesive, such as spray glue. However, such lamination techniques typically involve only a partial application of adhesive over some predefined patterned area of spots or other shapes on selected portions of the belt layers, with the remaining areas of the belt layers not bonded with adjacent layers and therefore free to move relative to these adjacent layers. As a result, the layers remain substantially independent and subject to manipulation by shear forces. Further, the physical properties of the laminated belt cannot be modified over different areas of the belt. Additionally, because the layers are not integrated together and are free to move, they add unnecessary volume and bulk to the belt assembly. Glued belt assemblies are also typically not water resistant due to the partial water solubility of the adhesive. Thus such belt assemblies often also employ stitching techniques to attempt maintain their integrity upon failure of the lamination. The added stitching requirement makes the assembly process time-consuming and may result in one or more of the further disadvantages described above.

These and other shortcomings are addressed in the present disclosure.

SUMMARY

In an aspect of the disclosure, an orthopedic back brace includes a spinal support element and at least one belt member coupled to the spinal support element for securing the spinal support element to a user, wherein the at least one belt member comprises a plurality of materials thermally fused together to form a unitary segment.

In another aspect of the disclosure, an orthopedic back brace includes a spinal support element including an anterior portion of a posterior pad configured for placement against a spinal area of a user, and at least one belt member, coupled to the spinal support element, for extending around a user's torso to assist in securing the spinal support element in place, wherein the at least one belt member comprises a plurality of thermally fused materials configured to form a unitary segment.

In another aspect of the disclosure, an orthopedic back brace includes a spinal support element, and two belt members coupled to the spinal support element and configured to secure the spinal support element onto a user, wherein at least portions of the two belt members include materials thermally fused together to integrate the materials into a single segment.

In another aspect of the disclosure, an orthopedic back brace includes a spinal support element comprising an anterior portion of a posterior pad configured for placement against a spinal area of a user, and at least one belt member coupled to the spinal support element and configured to secure the spinal support element onto a user, wherein the anterior portion comprises a plurality of materials thermally fused together to form a unitary segment.

In another aspect of the disclosure, the orthopedic back brace as described above includes a posterior portion of the posterior pad, wherein the posterior portion includes at least two materials thermally fused together.

It is understood that other aspects will become readily apparent to those skilled in the art from the following detailed description, wherein it is shown and described only exemplary configurations of a flexible support by way of illustration. As will be realized, the present disclosure includes other and different aspects of a flexible support and its several details are capable of modification in various other respects, all without departing from the spirit and scope of the present disclosure. Accordingly, the drawings and the detailed description are to be regarded as illustrative in nature and not as restrictive.

BRIEF DESCRIPTION OF THE DRAWINGS

Various aspects of the present invention are illustrated by way of example, and not by way of limitation, in the accompanying drawings, wherein:

FIG. 3 shows a front posterior view of the orthopedic back brace of FIG. 1 with the posterior cover, posterior frame and posterior cover material removed.

FIG. 4 shows a close-up front view of the pulley system.

FIG. 14A discloses a front posterior view of the belt member of the orthopedic back brace.

FIG. 14B discloses a front anterior view of the belt member of the orthopedic back brace

FIG. 16A is a front posterior view of a belt member.

FIG. 16B shows a cross-sectional view of the belt member of FIG. 16A along plane A-A.

FIG. 16C shows a cross-sectional view of the belt member of FIG. 16A along plane B-B.

FIG. 16D shows a perspective view of the belt member of FIG. 16A.

DETAILED DESCRIPTION

Figure 1:
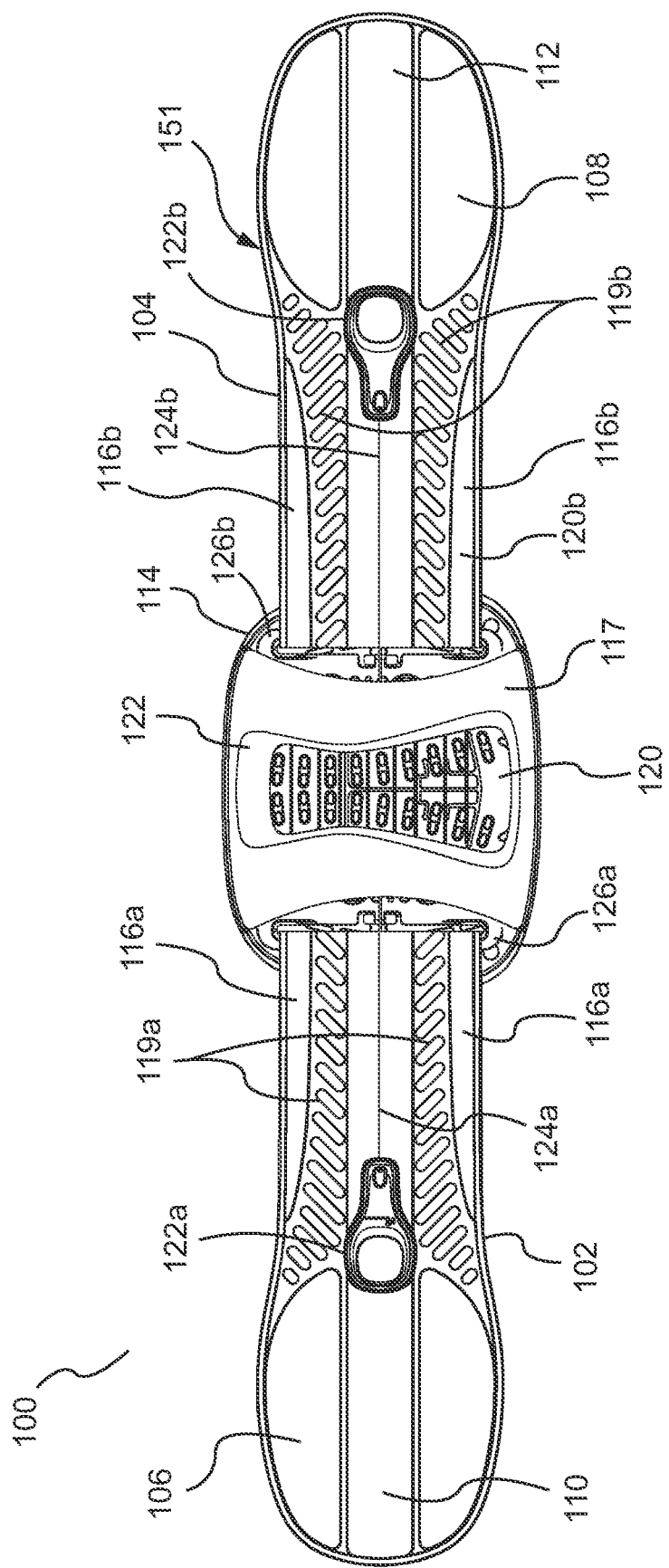
FIG. 1 is a front posterior view illustrating an example of an orthopedic back brace according to the present disclosure.

Various aspects of an orthopedic back brace will now be presented. However, as those skilled in the art will readily appreciate, these aspects may be extended to other anatomical supports without departing from the spirit and scope of the present disclosure. The detailed description set forth below in connection with the appended drawings is intended to provide a description of various exemplary embodiments of techniques for an orthopedic back brace and is not intended to represent the only embodiments in which the invention may be practiced. The term "exemplary" used throughout this disclosure means "serving as an example, instance, or illustration," and should not necessarily be construed as preferred or advantageous over other embodiments presented in this disclosure. The detailed description includes specific details for the purpose of providing a thorough and complete disclosure that fully conveys the scope of the invention to those skilled in the art. However, the invention may be practiced without these specific details. In some instances, well-known structures and components may be shown in block diagram form, or omitted entirely, in order to avoid obscuring the various concepts presented throughout this disclosure. The various aspects of the present disclosure illustrated in the drawings may not be drawn to scale. Rather, the dimensions of the various features may be expanded or reduced for clarity. In addition, some of the drawings may be simplified for clarity. Thus, the drawings may not depict all of the components of a given apparatus or method.

In accordance with various aspects of the present disclosure, a welded orthopedic back brace is provided. In one aspect, the back brace includes one or more belt members having materials thermally fused together to integrate the materials to form the one or more belt members. The use of thermal fusion to create the belt members provides for a number of advantages over conventional techniques. As an example, the welded nature of the belt members integrates the belt materials together in a manner such that the corresponding belt member form a single, unitary segment. This is in contrast to conventional techniques, most of which use sewing or stitching of a number of essentially independent layers to form the belt members.

In these conventional techniques, as discussed briefly above, often two or more materials are placed on or adjacent each other and are sewn longitudinally along the belt borders or in other locations on the belt member. As a result of this configuration, conventional belt members tend to cause a user unnecessary discomfort, particularly when worn for long periods of time. This is in part because the materials are only attached together at specific stitching points and as such, the materials tend to separate in areas away from those specific stitching points. To this end, the various materials of the belt tend to act individually and/or independently of each other, as described above. That is, when the back brace is donned by a user and the belt is fit snugly around the user's waist, the materials often bunch up in undesirable areas and otherwise move in unpredictable ways.

Among other problems, these phenomena generally cause discomfort to the user by adding various pressure points where the material is thickest or in areas where the material has congregated when the belt is worn. The discomfort can be exacerbated in belts that are stitched at or near sensitive parts of a user's anatomy. For example, the stitched borders may in some cases exert substantially more pressure on a user's waist than in areas where less or no stitching is present. In apparent recognition of these deficiencies, practitioners have made various efforts to address them by adding additional layers or thickness to the belt in an effort to reduce discomfort.

However, the addition of extra layers as an attempted solution tends to ultimately make the stitched belt members unnecessarily voluminous. Each layer of material that constitutes a portion of the belt member is generally an individual piece of material and as such, contributes to the overall volume of the belt. The volume of the belt is something which can exacerbate problems with users who are self-conscious about wearing such devices in public. In many cases, the volume of these conventional belts is so large that it is not practicable for a user to wear attire over the belt. Rather, the belt must be worn externally, which can contribute to the negative perceptions sometimes associated by users with such orthopedic devices.

Still other conventional solutions involve the use of a laminate or adhesive such as spray glue over partial regions of the belt layers which, as described above, tends to add unnecessary cumulative volume to the belt and renders it difficult if not impossible to control critical properties of the belt across specific areas. Further, as indicated above, laminated belt assemblies include substantially independent belt layers that remain subject to shear forces and glue failures. These conventional solutions also tend to produce abrupt discontinuities in areas where the layers change (e.g., where a layer is removed or thinned), more often than not resulting in noticeable user discomfort.

In addition, the belt members serve very important functions in the overall device—for example, to enable a secure but comfortable fit of the posterior in order to straighten the spinal column. To accomplish this function, the materials selected for use in the belt members and their characteristics (thickness, elasticity, solidity, rigidity, firmness, volume, etc.) generally must be carefully selected in order to achieve a specific set of results for the belt, depending on the user or the application. For example, the belt members generally need to use materials that include properties like elasticity, rigidity, stiffness, etc., in order to both be efficacious and to provide comfort to the user. In conventional back braces, this process is often accomplished by selecting materials having entirely different properties and by stitching the disparate materials together. As a result, there often exists a significant gradient in areas of the belt member where the materials, and hence the belt properties, change, which in turn is an effect felt by the user. For instance, many conventional back braces stitch an elastic material to a rigid material. The sharp difference in elasticity on one portion of the belt (and consequently on one portion of the user's body) and rigidity on another immediately adjacent portion of the belt can be fairly conspicuously felt by a user, and is an added discomfort. Yet another problem with this approach is that, more often than not, it is difficult to obtain a predictable set of combined properties across specific regions of the belt materials that would render the belt assembly an optimal solution for a specific orthopedic application.

In contrast to these techniques, with respect to certain embodiments to be discussed below, at least a portion of the belt materials are welded together. That is, rather than exclusively using stitching or another method, at least a portion of the belt materials are thermally fused to essentially form a single, unitary segment. Because the belt materials are thermally fused instead of sewn, the belt members have a naturally low profile with a compact volume that tends to be much smaller than existing solutions. As described below with reference to FIG. 15, thermal fusion produces an overall compression of the constituent materials. Further, using the thermal fusion process as described herein, it is generally easier for a developer to accurately design and achieve predictable and continuous properties over specific areas or regions of the belt. This is in part due to the fact that the belt behaves as a unitary segment rather than as a collection of individual materials with substantially different properties and different degrees of directional freedom. As described in greater detail below, welding the materials causes the materials to become permanently affixed together across all welded regions, in contrast to the conventional approaches that rely purely on stitching or lamination.

Additionally, the back brace according to the present disclosure tends to avoid sharp gradients in property transitions of materials. This benefit is due to the ability of thermal welding to integrate the fused materials together. For example, when a segment of a generally rigid material is thermally fused with a segment of generally elastic material, the area corresponding to the thermal fusion typically has properties that include the properties of both of the fused materials—namely, some amount of elasticity and some amount of rigidity. This gradual transition of material properties, rather than sharp gradients produced by conventional means, generally results in a much more comfortable user experience. This, combined with more compact and lower profile belt members, results in a back brace that is far more likely to be worn by a user as recommended by a medical professional.

FIG. 1 is a front posterior view illustrating an example of an orthopedic back brace 100 according to the present disclosure. FIG. 1, more specifically, shows an outer view of the back brace 100, i.e., away from a user's waist. The back brace 100 in this embodiment shows belt members 102 and 104 respectively coupled to a spinal support element 114 via D-rings 126a and 126b. Although for purposes of this embodiment two belt members are utilized, a single belt maybe be equally suitable. Further, while the D-rings coupling the belt members are discussed in greater detail below, it should be understood that the belt members may generally be coupled to the spinal support element 114 in any suitable way. In some embodiments in which a single belt member is utilized, the belt member may be movably or non-movably coupled to the spinal support element 114 via a slit or other connection mechanism.

Spinal support element 114 generally includes a posterior cover 117, posterior cover window 122 and posterior cover material 120. In one exemplary embodiment, the outer part of posterior cover 117 is composed of thermoplastic polyurethane (TPU) and the posterior cover material 120 is a mesh material. In another exemplary embodiment, the cover material 120 is substantially transparent and has breathable properties for enabling airflow into spinal support element 114. Each of belt members 102 and 104 include respective belt end segments 106 and 108. In one embodiment, belt end segments 106 and 108 are composed of unbroken loop material (UBL). In another embodiment, only belt end segment 106 is composed of UBL and is used to engage with an opposing segment on an anterior side of the belt, as shown with reference to FIG. 2. In other embodiments, belt end segments 106 and 108 are composed of another suitable material. In still other embodiments, belt end segments 106 and 108 may have different shapes, or simply end on one or both sides in a rectangular shape corresponding to the remainder of the belt shape of the belt members 102 and 104. Belt end segments 106 and 108 constitute squares, rectangles, ellipses, or any other shape.

Belt members 102 and 104 also include an exterior layer 119a on one side (belt member 102), and 119b on the other side (belt member 104). In an exemplary embodiment, exterior layers 119a-b are composed of TPU. Further, in this embodiment, exterior layers 119a-b include a series of angled oblong capsule-like shapes that run longitudinally along belt members 102 and 104. It should be noted that different structures composed of the same material may have different thicknesses and other properties and may be composed of other or different elements or combinations thereof.

Belt member 102 further includes winged members 116a on belt member 102 and 116b on belt member 104. In an exemplary embodiment, winged members 116a-b are also composed of UBL. Belt members 102 and 104 may also include regions 110 and 112 of material that extend longitudinally thereacross. In an exemplary embodiment, regions 110 and 112 are composed of UBL. In this embodiment, UBL is provided to enable hook material disposed on pull rings 122a and 122b to attach to regions 110 and 112, respectively, so that they can be secured and easily located as necessary by a user. However, in other embodiments regions 110 and 112 may be composed of hook material or another suitable material. It will be appreciated that these details of the belt members 110 and 112 are for purposes of illustration and that many different types, shapes and configurations of materials may be contemplated.

Affixed to belt members 102 and 104 can further be seen pull rings 122a and 122b. The pull rings are used to provide tension to a pulley assembly (obscured from view) via pulley ropes 124a and 124b. In other embodiments, only a single pull ring may be more suitable. As described further below, the pull rings 122a-b enable a user to make microadjustments to the fit of the back brace.

Figure 2:
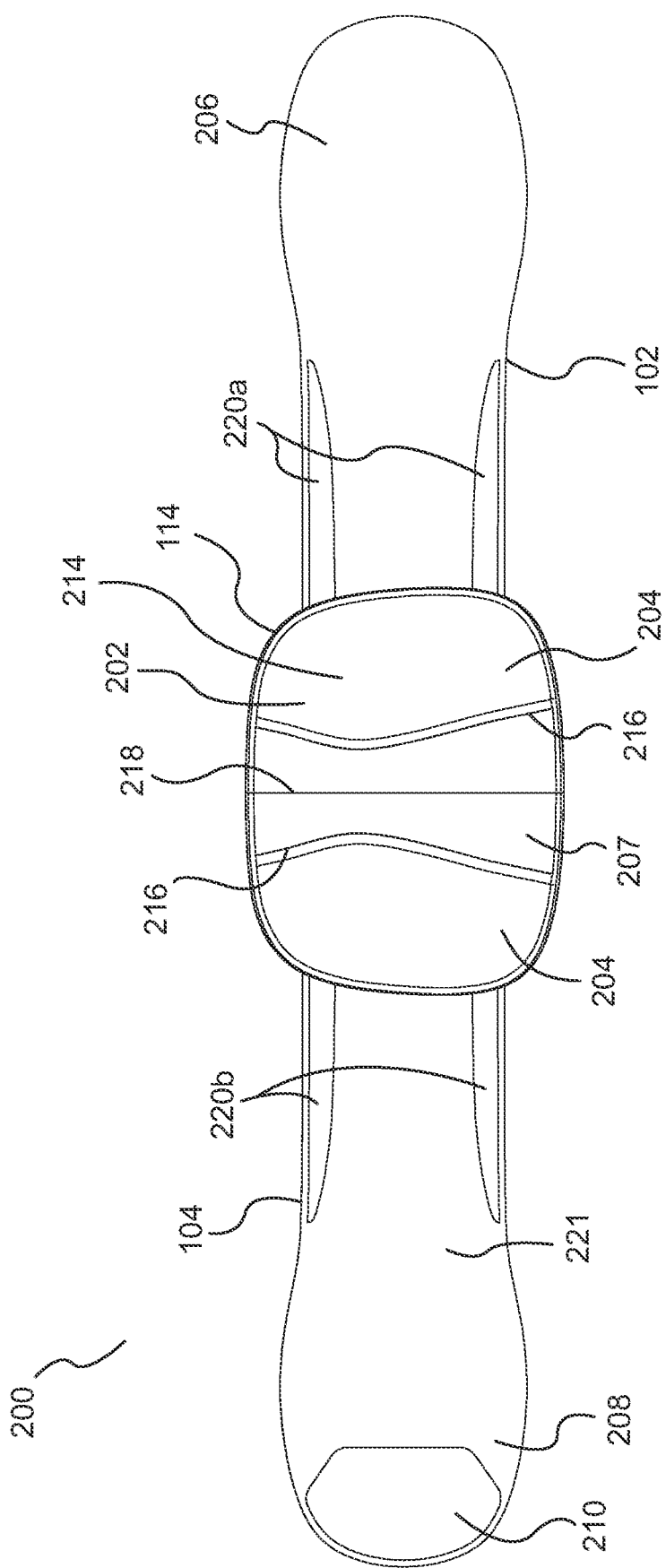
FIG. 2 is a front anterior view illustrating an example of an orthopedic back brace of the present disclosure.

FIG. 2 is a front anterior view illustrating an example of the orthopedic back brace shown in FIG. 1. FIG. 2 includes an anterior view of spinal support element 114. In this embodiment, spinal support element 114 includes a posterior pad 202 configured to comfortably rest flush against a designated spinal region of a user. Thus, from the figure, an anterior portion 214 of the posterior pad 202 is visible. While the embodiment shown in FIG. 2 includes a spinal support element 114 having a posterior pad 202 as one component of the spinal support element 114, it will be appreciated that spinal support element 114 need not be so limited and may be configured in a number of ways depending on the user's needs.

Posterior pad 202 further includes pad spacer section 204 and pad mesh element 207. In one exemplary embodiment, pad spacer section 204 constitutes a single pad of 3-D spacer mesh material overlaid by the pad mesh element 207. While any number of materials can be suitably used, 3-D spacer mesh material is known for its comfort, cushioning, strength, breathability design efficiency, and versatility. Posterior pad 202 is further composed of mesh section 207. In an exemplary embodiment, mesh material is used in section 207 to ensure comfort and breathability. These considerations are especially significant given that in this embodiment, section 207 may rest substantially flush against the spinal area of a user. The user, in turn, may be experiencing pain, or may have recently had spinal surgery in this region. The use of mesh in section 207, and 3-D spacer in section 204, assists in providing more comfort to the user than existing solutions. In other embodiments, the entire anterior portion 214 of posterior pad 202 may be made of a single material, such as mesh. In one aspect of the disclosure, the mesh section 207 and the respective pad spacer elements 204 may be coupled together at segments 216 via a thermal fusion process as described further below with reference to FIG. 8.

Referring still to FIG. 2, the anterior portion of belt members 102, 104 are shown and include belt end segments 206 and 208, which correspond respectively to belt end segments 106 and 108 of FIG. 1. In one embodiment, the material of the anterior portion 221 of belt members 104 and 102 and belt end segments 206 and 208 may be composed of a 3-D spacer mesh material for providing a user with comfort, durability and cushioning. Additionally, associated with belt end segment 208 is a connection portion 210. In one embodiment, connection portion 210 on belt member 104 may be composed of hook material. Connection portion 210 thereby enables the user to securely affix the belt around the user's waist or torso by securely engaging the hook material of the connection portion 210 with the UBL material on the opposing belt member 102 other side of the belt, i.e., in sections 106 and 110 (see FIG. 1). It is noted again that while specific configurations of hook and UBL material are recited, these details are presented for purposes for illustration and are not intended to limit the scope of the invention. In other embodiments, for example, another equally suitable connection means may be employed in lieu of hook and loop material.

Each of belt members 102 and 104 in FIG. 2 further include winged members 220a on belt member 102 and 220b on belt member 104. In an embodiment, the winged members 220a-b are composed of UBL.

FIG. 3 shows a front posterior view of the orthopedic back brace of FIG. 1 with the posterior cover 117, posterior cover window 122 and posterior cover material 120 removed. As is more readily apparent from this view, belt members 102 and 104 are coupled to spinal support element 114 via a pulley system 302 and D-rings 126a and 126b. More specifically, in this exemplary embodiment, belt member 102 is threaded through D-ring 126a and is coupled to an anterior side of the belt member 102 via a hook and loop connection. Thus, for example, an anterior side of the belt member 102 may contain areas of hook material closer to the inner anterior edge (not shown) of belt member 102 that mate with the UBL material on winged members 220a (see FIG. 2). Similarly, in this embodiment, belt member 104 is threaded through D-ring 126b and is coupled to an anterior side of the belt member 104 via a hook and loop connection. For example, an anterior side of the belt member 104 may also contain areas of hook material closer to the inner anterior edge of belt member 104 that mate with the UBL material on winged members 220b. These embodiments are described further with respect to FIGS. 9A-C, below.

Thus, more simply, belt members 102 and 104 in this embodiment are securably coupled to spinal support element 114 via their fold-over hook and loop connection on the anterior side of the belt members 102 and 104. It will be appreciated that other embodiments may be equally suitable for coupling the belt members to the spinal support element. For example, the belt members 102 and 104 may in alternative embodiments be permanently affixed to spinal support element 114, via D-rings 126a and 126b or otherwise. In other embodiments, the belt members 102 and 104 may be threaded through D-rings 126a-b such that the belt mates via a hook and loop connection on the posterior side rather than the anterior side, as shown. Numerous other arrangements may be equally suitable depending on the application and objectives.

FIG. 3 further shows that D-rings 126a-b are coupled to spinal support element 114 via a pulley system 302 (FIG. 4). Also shown in FIG. 3 as part of spinal support element 114 is posterior frame 304. In one embodiment, posterior frame 304 comprises a plastic pad designed and shaped to fit the contour of the spinal region of a user of a particular size. Posterior frame 304 may include a specific amount of rigidity so as to adequately influence a position, and/or maintain a proper alignment, of the spinal column of a user. Posterior frame 304 includes a plurality of capsule-shaped orifices 306 and 308 disposed across back pad 304 and configured to provide breathability. The use of orifices 306 and 308 may also influence the flexibility of posterior frame 304. In general, posterior frame 304 is composed of a material having a thickness and geometrical shape that is suitable for providing the requisite spinal support given the medical or orthopedic application.

In some embodiments, posterior frame 304 may include, or be coupled to, one or more additional pads positioned between posterior frame 304 on one hand, and posterior pad 202 (FIG. 2) on the other hand, for further support and to provide additional levels of cushioning and breathability. For example, posterior frame 304 may overlay another foam back pad and/or back wing section which is then covered by posterior pad 202 (FIG. 2). In one embodiment, to provide a layer of extra comfort with breathability, a foam pad with orifices (FIG. 11) is inserted between the posterior frame 304 and posterior pad 202. The details and configuration of the back panels may, in short, vary in accordance with the embodiment and application.

FIG. 4 shows a close-up front view of the pulley system 302 in accordance with the present disclosure. In one embodiment, the D-rings 126a and 126b of pulley system 302 are respectively coupled to posterior frame 304 via any suitable connection means, such as a direct plastic connection or a slidable connection using plastic protrusions slidably engaged with slits in posterior frame 304, etc. As discussed above, once a user has donned the back brace and engaged the belt member at the front of the user's body, the user can provide micro-adjustments to the fit of the back brace by pulling on pull rings 122a and 122b, which in turn provides tension to pulley ropes 124a and 124b. Pulley rope 124a is threaded through guide 412 and winds around various sections of pulley posts 404 before termination at the anchor 408. Similarly, pulley rope 124b is threaded through guide 410 and winds around various sections of pulley posts 402 before being terminated at anchor 406. Using the pulley system as is conventionally known, the tension on the pulley ropes 124a-b causes the D-rings to exert lateral forces on spinal support element 114 (or components thereof) such that the spinal support element can be more securely tightened across the user's spinal region. The D-rings 126a-b may be (slidably coupled) to posterior frame 304 for engaging the back pad 304 in response to tension from pulley ropes 124a-b, as discussed further below.

In alternative arrangements, a single pulley rope may be used to provide the force to tighten the back brace. In still other configurations, a pulley system is not employed, and the belt members are coupled directly to spinal support element 114 and adjustment is performed by the user providing tension directly to the belt member(s).

Figure 5:
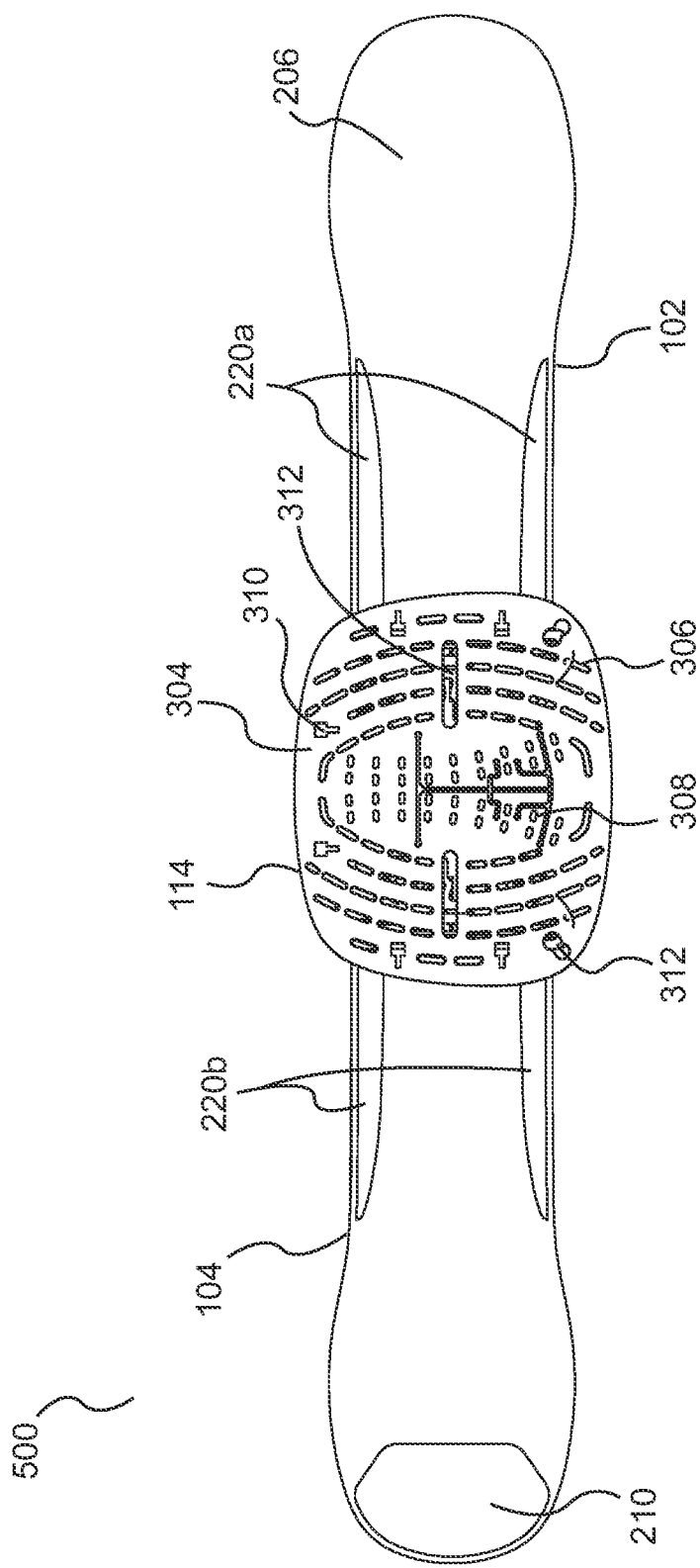
FIG. 5 shows an anterior view of the orthopedic back brace with the posterior pad removed.

FIG. 5 shows an anterior view of the orthopedic back brace 500 with the posterior pad 202 (FIG. 2) removed. An anterior side of posterior frame 304 (FIG. 3) is shown. Posterior frame 304 includes orifices 306 and 308 for breathability and for accommodating various design considerations as known in the art. Posterior frame 304 may be secured to other components of spinal support element 114 via attachment openings 310 or other suitable methods. Horizontally disposed orifices 312 are, in an embodiment, used to enable a connection to D-rings 126a-b (FIG. 4). More specifically, the underside of D-rings 126a-b (relative to a viewer of the posterior side of the back brace (FIG. 1)) may include plastic extrusions that protrude through orifices 312 and are secured on the opposite side of the orifices by flaps or other elements. This configuration enables D-rings 126a-b to be slidably coupled to posterior frame 304 and to engage and tighten the posterior frame 304 when tension on the pulley strings 124a-b is provided. Orifices 312, in some embodiments, may provide further positive design characteristics, may be used with connectors, and/or may beneficially affect the bendability of the spinal support element 114. As indicated above, in other embodiments spinal support element 114 may include additional layers or components made of plastic, foam or other material disposed between posterior frame 304 and posterior pad 202. For example, a 3-D spacer mesh wing pad and/or another foam pad (FIG. 11) may be used to add additional breathable comfort to accommodate various design considerations.

Figure 6:
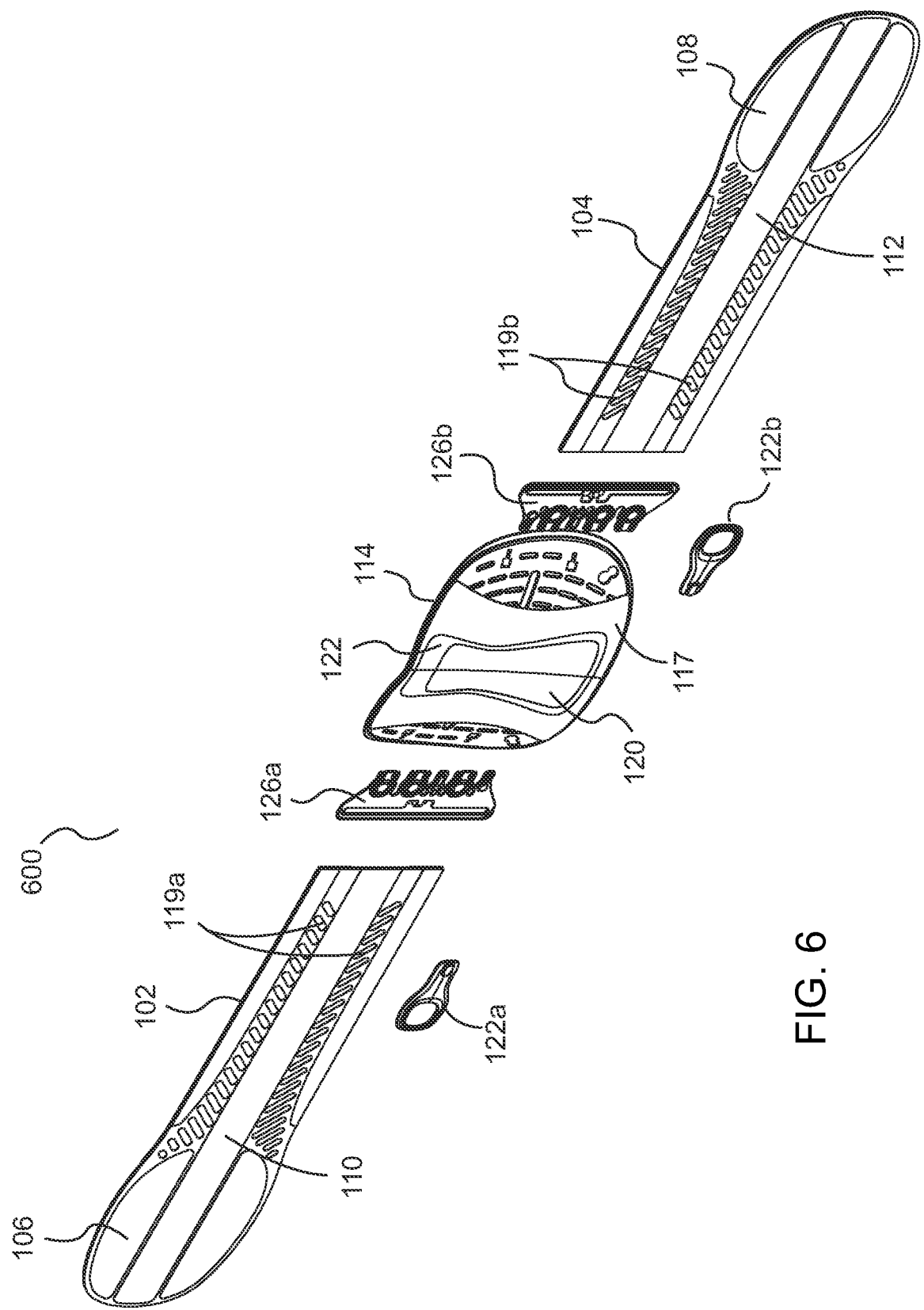
FIG. 6 shows a perspective posterior view of the orthopedic back brace according to the present disclosure.

FIG. 6 shows a perspective posterior view of the orthopedic back brace 600 according to the present disclosure. Portions of back brace 600 have been disassembled for clarity. Belt members 102 and 104 are coupled respectively to spinal support element 114 via D-rings 126a-b and pulley system 302 (FIG. 3). Also shown is exterior layer 119a-b disposed longitudinally across the respective belt members 102 and 104. Further shown is posterior cover 117, posterior cover window 122, and posterior cover material 120. In an embodiment, posterior cover 117, posterior frame and posterior cover material 120 are welded together via a thermal fusion process as described herein.

Figure 7:
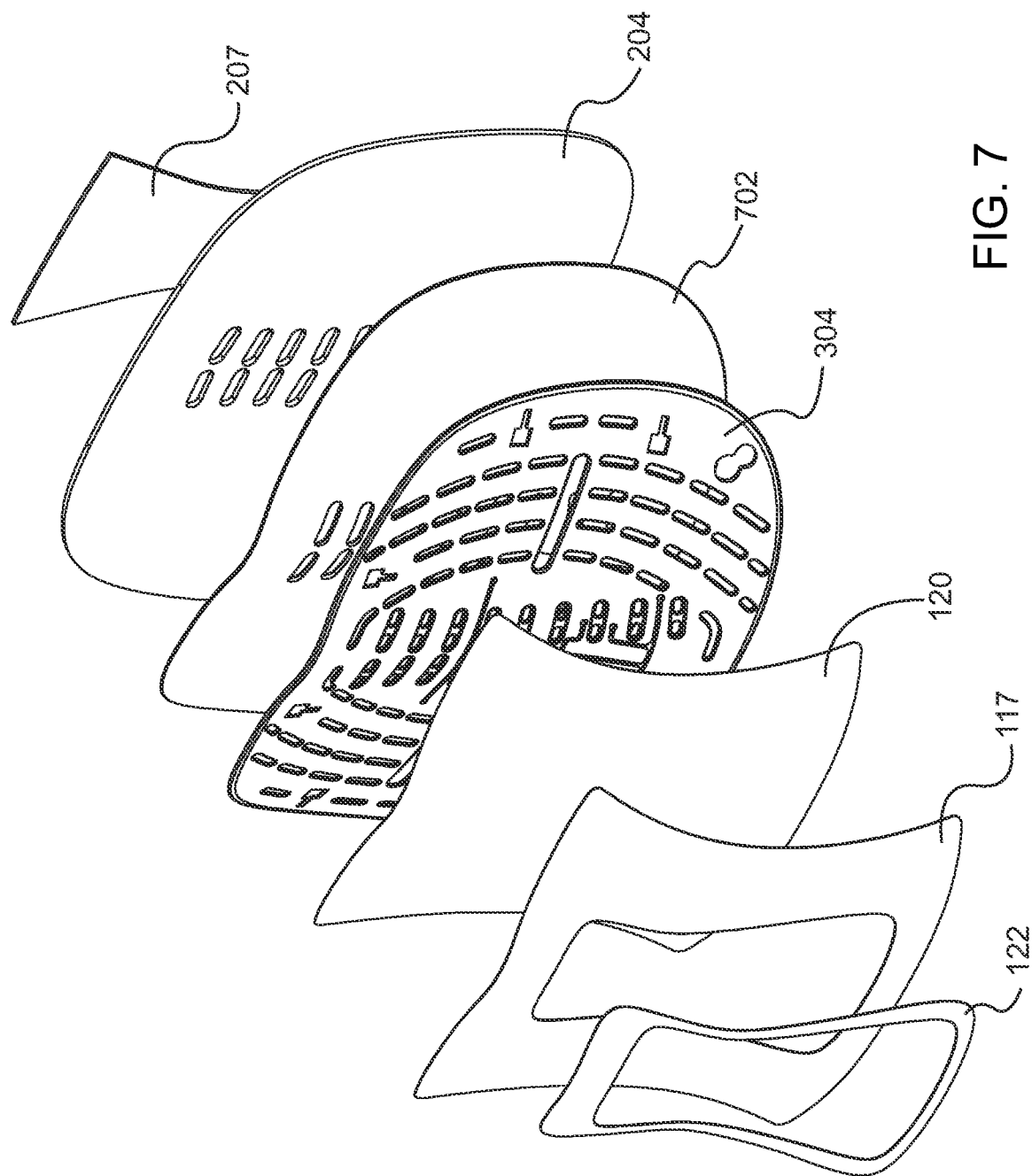
FIG. 7 shows a perspective staggered view of exemplary elements of a spinal support element and their relative order and orientations.

FIG. 7 shows a perspective staggered view of exemplary elements of a spinal support element 114 and their relative order and orientations according to an exemplary embodiment. Thus, FIG. 7 illustrates how the various components may be stacked together to form spinal support element 114. These details are illustrative in nature and a large number of different embodiments using more or substantially less layers of elements or materials may be equally suitable in other embodiments.

Towards the left side of FIG. 7, the components comprising the posterior portion of spinal support element 114 are shown (i.e., that portion opposite the user's back). Similarly, towards the right side of FIG. 7, the components comprising the anterior portion of spinal support element 114 are shown. That is to say, certain components are configured to be flush against a user's back as set forth in greater detail below.

Starting from the left, posterior cover window 122 may be affixed to posterior cover 117. In turn, posterior cover 117 may be affixed to posterior cover material 120. In various embodiments, two or more of posterior cover window 122, posterior cover 117 and posterior cover material 120 are thermally fused together to form a more compact and integrated posterior cover of spinal support element 114, which eliminates the need for stitching. In other embodiments, stitching or adhesives may be use to combine these materials. In still other embodiments, the entire network of materials or some portion thereof may be welded together to form a unitary sleeve or cover.

Posterior cover material 120 is thereupon shown adjacent posterior frame 304 (FIG. 3). It should be noted that the pulley assembly 302 and associated D-rings 126*a-b* are not shown here for ease of clarity. However, as discussed above, D-rings are generally coupled to a surface of posterior frame 304. Referring still to FIG. 7, posterior frame 304 is affixed flush against foam pad 702. In an embodiment, foam pad 702 is an open cell foam or styrene foam material used to provide cushioning and breathability for the user. Foam pad 702, in turn, is secured to pad spacer section 204, which is affixed to pad mesh element 207. Pad spacer section 204 and pad mesh element 207 form an anterior portion of posterior pad 202 of spinal support element 114, which anterior portion rests flush against a user's back.

Generally, one or more of the structures of FIG. 7 may be included in the spinal support element 114. The elements may be affixed or attached to one another in a variety of ways. In some exemplary embodiments, one or more of the elements of FIG. 7 are placed flush against each other with no direct connection. In other embodiments, one or more of the elements of FIG. 7 are affixed together at or near respective border areas of the elements, or other areas. The manner of connection may vary widely and may involve one more of adhesives, thermal fusion as herein described, clamping mechanisms, or other hardware elements used for connection means.

In an exemplary embodiment, posterior cover window 122 is composed of substantially transparent breathable mesh material that enables a viewer to observe the interior of the spinal support element 114. Posterior cover material 120 may also be substantially transparent such that a viewer can observe portions of the pulley system 302 and the posterior frame 304 via posterior cover window 122, as is most evident with reference to FIG. 1. This window and the transparent mesh material provides additional relief to the user because each layer of the structure of FIG. 7 provides breathability. The resulting spinal support element 114 consequently enables air to flow from an area external to posterior cover window 122 via the various structures to the user's affected area, which may reduce itching and irritation and risk of skin infection, and which may promote healing. This is in contrast to conventional back braces in which the affected area may be substantially limited or altogether obscured from external exposure of air.

Figure 8:
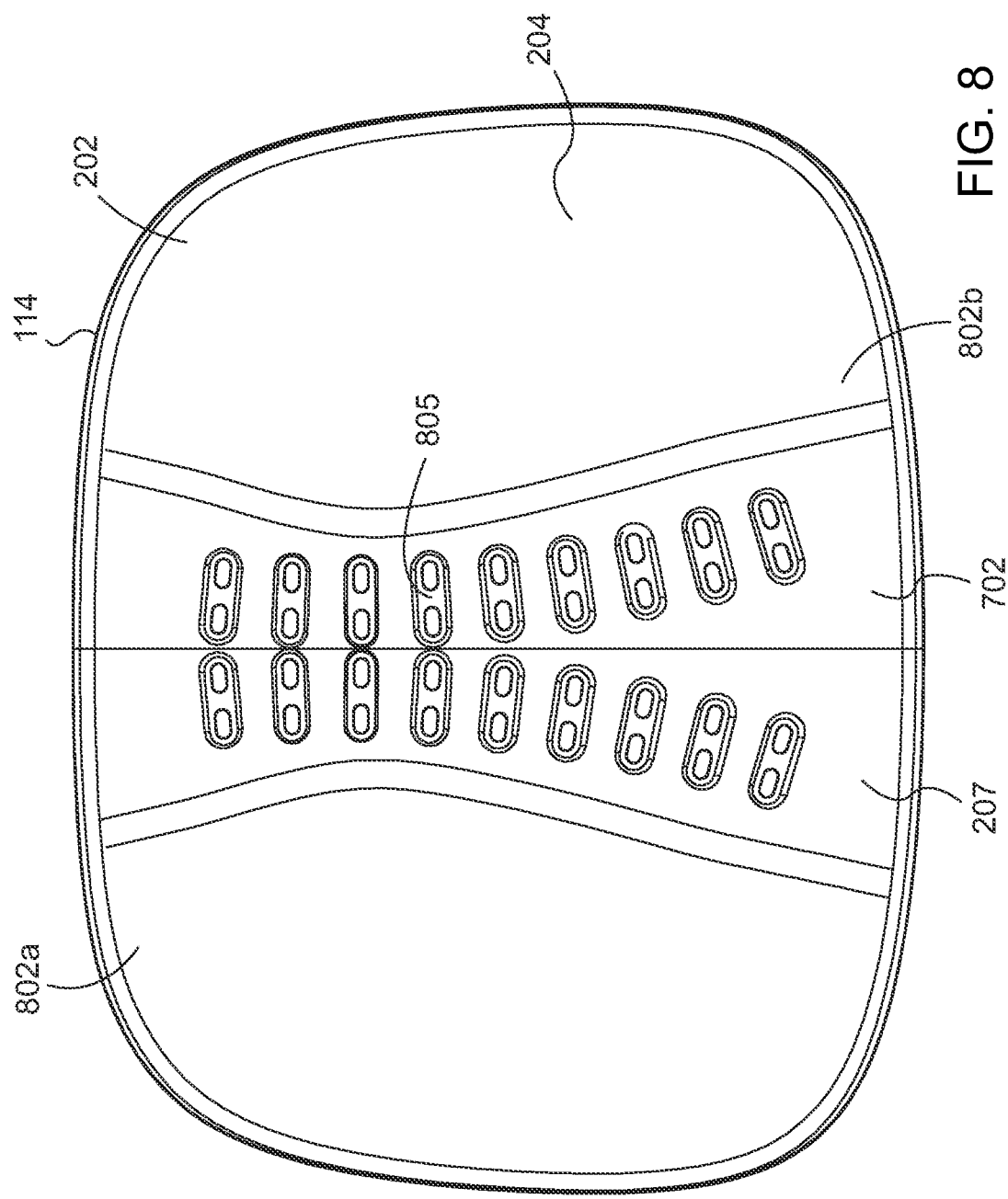
FIG. 8 shows an anterior view of the posterior pad of spinal support element of the orthopedic back brace of the present disclosure.

FIG. 8 shows an anterior view of the posterior pad 202 of spinal support element 114 of the orthopedic back brace. In this embodiment, spinal support element 114 includes a posterior pad 202 composed of pad spacer section 204 and pad mesh element 207. In one configuration, the materials are welded together using thermal fusion. For example, pad mesh element 207 is thermally fused along regions 802*a* and 802*b* to pad spacer section 204. Pad spacer section 204 may, in turn, be welded to other materials included in spinal support element 114 to create a thin, low profile support. For example, pad spacer section 204 may be thermally fused to foam pad 702 (FIGS. 7 and 11) and/or to posterior cover 117 on the other side of the spinal support element 114. In this latter embodiment, pad spacer section 204 may constitute a sleeve that is thermally welded at the borders of the spinal support element 114 to the posterior cover 117 on the posterior side of the spinal support element 114. Thus, in this embodiment, the materials on the anterior and posterior sides of spinal support element 114 may be at least partially welded together such that spinal support element 114 is a substantially integrated and unitary component.

Referring back to FIG. 8, two strips of material 802*a* and 802*b* are used both to define the borders between pad spacer section 204 and pad mesh element 207 and to facilitate the thermal fusion process by acting as an intermediate or filler material, as discussed further below. In an exemplary embodiment, the strips of material 802*a-b* are composed of UBL, although various other materials may be equally suitable.

The use of welded materials on the anterior portion of posterior pad 202 of spinal support element 114 provides numerous advantages. For example, pad spacer section 204 may be welded to the pad mesh element 207 using another material, such as a thin strip of UBL tape disposed along segments 802*a-b*, to facilitate a weld having a smooth and comfortable transition. This feature is in contrast to conventional techniques which use stitching on the posterior pad. The use of stitching causes small but noticeable "bumps" or rigid protrusions in the material along the borders of the stitched materials. Since the anterior portion of the posterior pad 202 is flush against a user's spine, the rigid protrusions resulting from stitching are usually noticeable and potentially uncomfortable for a user, especially after long periods of use. The welding, as discussed above, enables a smooth transition between pad mesh element 207 on one hand, and 3-D spacer elements 204 on the other hand, such that any rigid protrusion otherwise formed through a stitching process is eliminated.

More fundamentally, the welded nature of the materials helps provides a low profile, lightweight spinal support element. Welding the materials provides a manufacturer with the ability to use different materials together even if the materials have otherwise disparate properties. This is in contrast to conventional back braces, which typically are more limited in their use of materials. Manufacturers of these conventional braces generally must use thicker materials to avoid stretching problems, which only increases the bulk of the back brace. In the back braced described herein, by contrast, comfortable segments of various types of materials such as different mesh materials may be seamlessly bound together. The use of such porous materials provides further breathability and comfort to the user.

Still referring to FIG. 8, the welding of pad mesh element to 207 and pad spacer section 204 is such that foam pad 702 is partially visible via the window composed of pad mesh element 207 and pad spacer section 204. The capsule shaped orifices contained in the foam pad 702 may be visible, or partially visible, through the pad spacer section 204 and pad mesh element 207. Generally, the configuration of spinal support element 114 and its constituent components may vary in a number of ways depending on the application and objectives for the back brace and remain within the spirit and scope of the present disclosure.

Figure 9A:
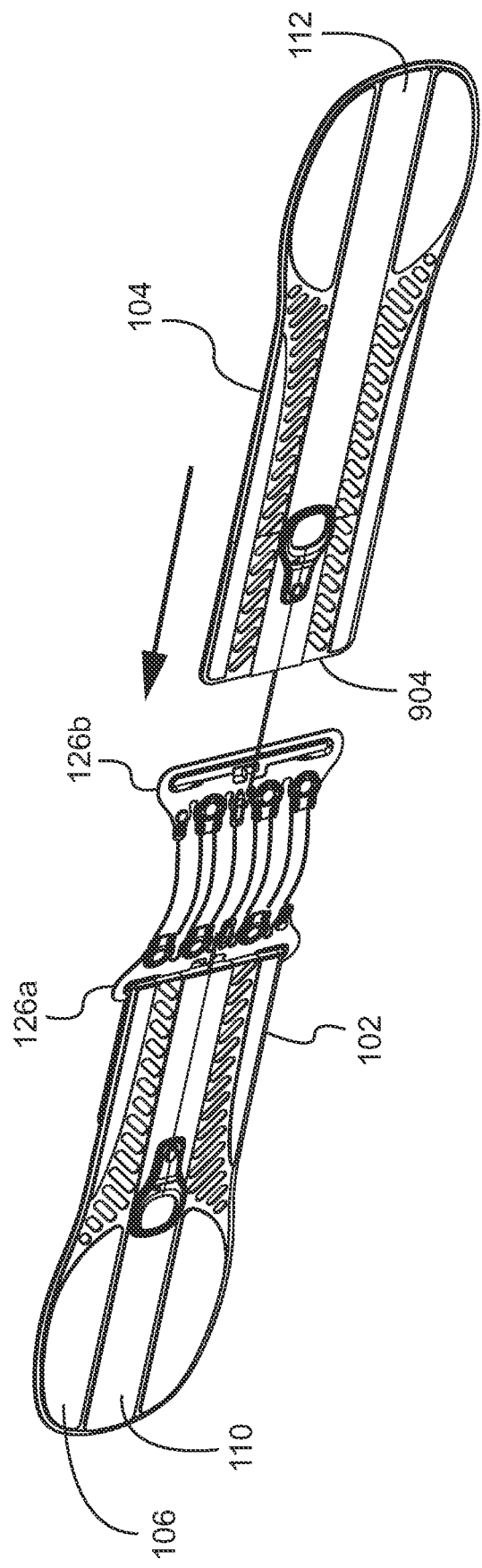
FIG. 9A shows a posterior perspective view of the orthopedic back brace having a belt member with an arrow indicating that the belt member is to be engaged with a D-ring.

Referring to FIG. 9A, an exemplary embodiment is shown for macro-fitting the belt around the waist of the user by using the end sections 902 and 904 of the belt members 102 and 104 proximate to the spinal support element 114. FIG. 9A shows a posterior perspective view of the orthopedic back brace having belt member 104 with an arrow indicating that belt member 104 is to be engaged with D-ring 126*b*. Thus, as part of a first step if the belt is not already assembled, a user or other professional can engage the belt members 102 and 104 with respective D-rings 126*a-b*.

Figure 9B:
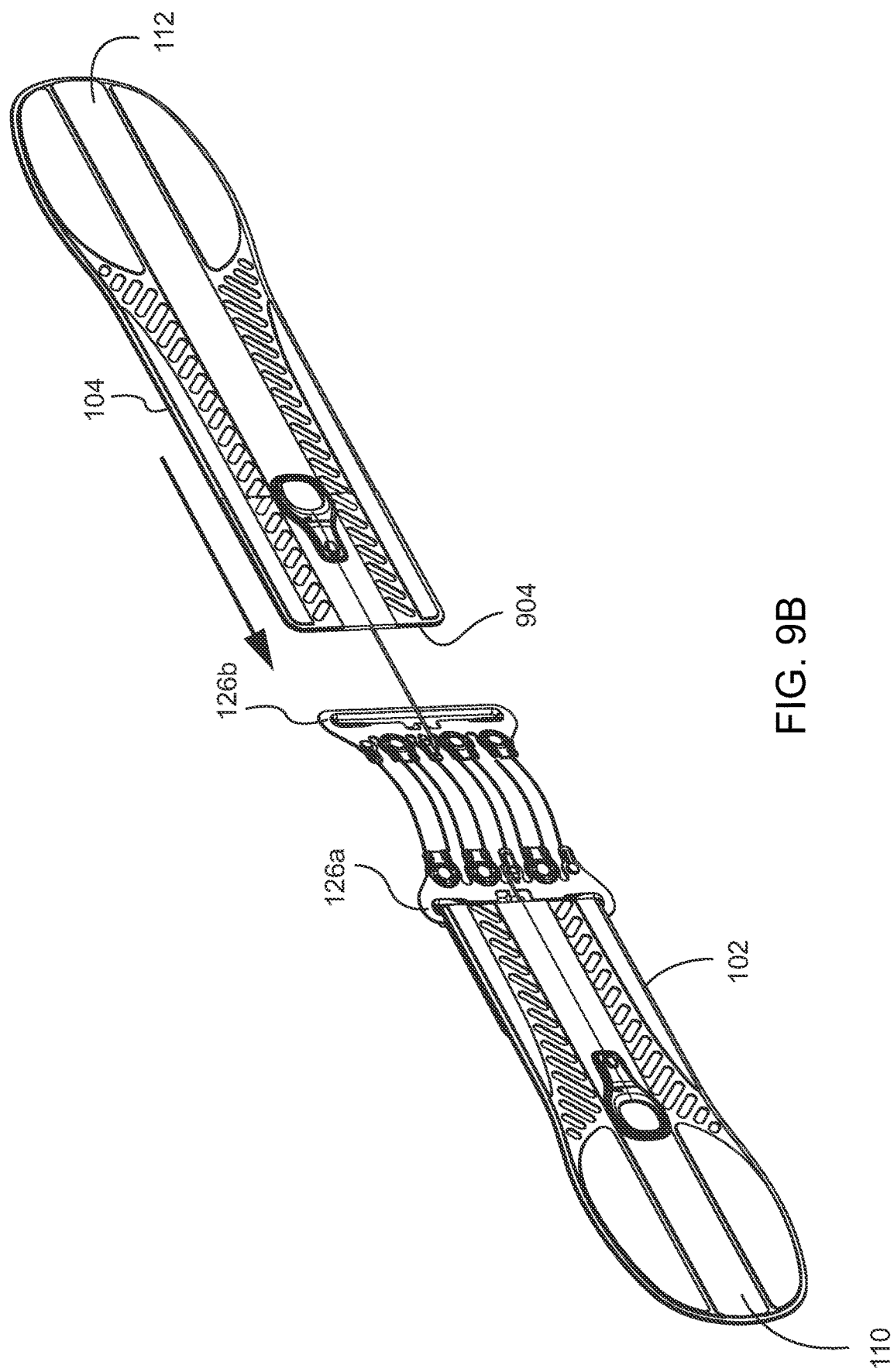
FIG. 9B shows a posterior perspective view of the same orthopedic back brace as FIG. 9A in an alternate orientation.

FIG. 9B shows a posterior perspective view of the same orthopedic back brace as FIG. 9A in an alternate orientation.

Figure 9C:
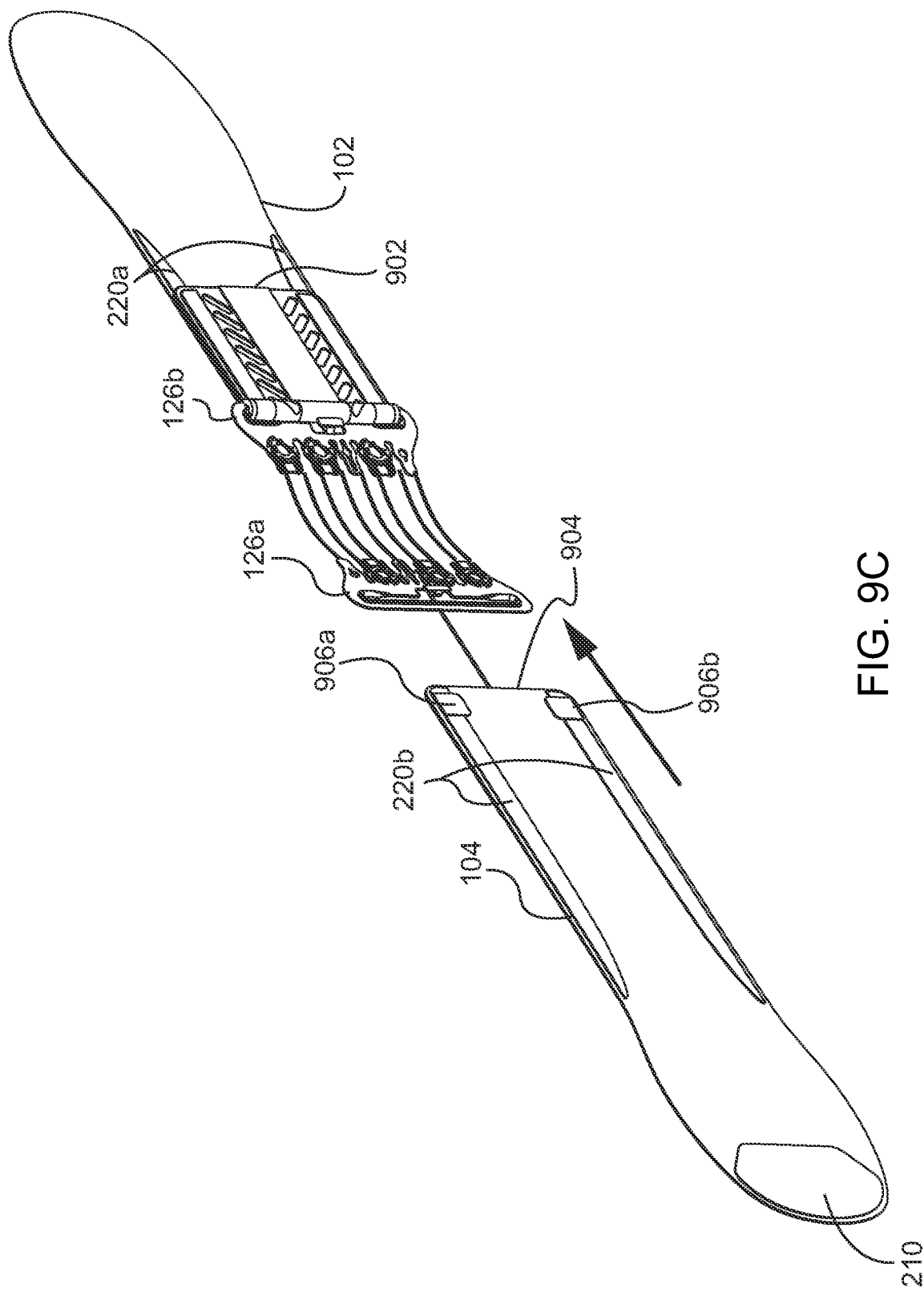
FIG. 9C shows an anterior perspective view of the same orthopedic back brace as FIG. 9A-B in another alternate orientation.

FIG. 9C shows an anterior perspective view of the same orthopedic back brace as FIG. 9A-B. The anterior portion of belt member 104 includes winged members 220*b*, which may be composed of a hook and loop material such as UBL. Further shown on belt member 104 are square-shaped regions 906a and 906b positioned near the end 904 of the belt member 104. In an embodiment, in a case where the winged members constitute UBL material, the corresponding squared sections 906a-b are composed of hook material and are ultimately used to engage with the winged members 220b to secure the belt at the correct macro-fit. FIG. 9C further shows belt member 102 already threaded through D-ring 126b and securely fastened via a hook and loop connection using similar hook squares on belt 102 to engage with the UBL winged members 220a.

Figure 10:
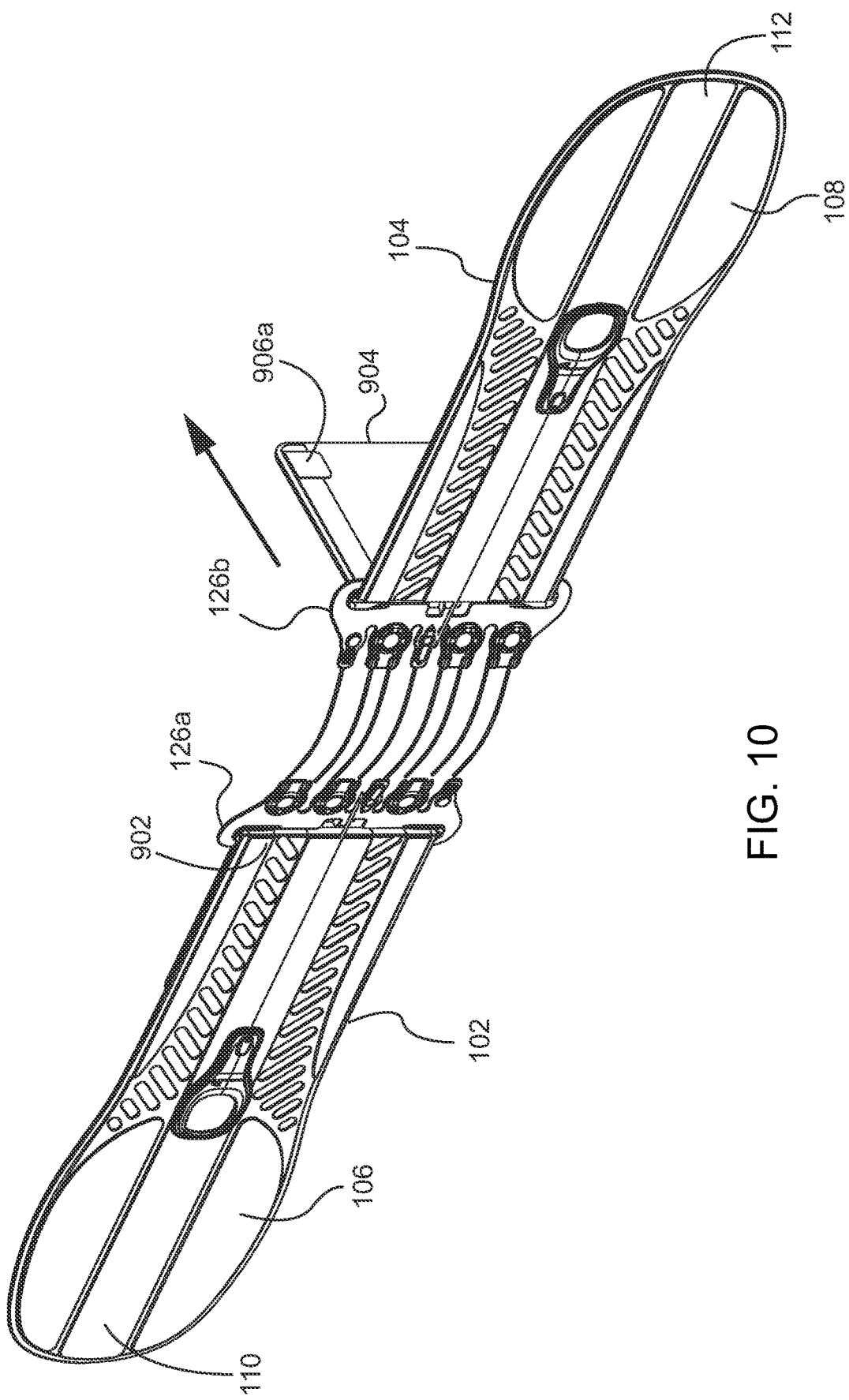
FIG. 10 shows a posterior perspective view of the back brace in the process of being threaded through the D-ring and being affixed via a hook and loop connection to an anterior portion of the belt.

FIG. 10 shows a posterior perspective view of the back brace in the process of being threaded through the D-ring 126b and being affixed via a hook and loop connection to an anterior portion of the belt (at winged members 220b (FIG. 9C)). It can be seen more clearly in FIG. 10 that in the embodiments of FIGS. 9A-C and 10, the belt end is threaded through D-ring 126b such that belt end 904 will be affixed to an anterior or inner portion of belt member 104. However, in alternate configurations, the belt members may fold through the D-rings 126a-b or other slit components in the opposite direction such that belt ends 902 and 904 and their respective hook sections 906a-b engage a posterior or outer side of the belt (such as engaging with UBL on winged members 116b in FIG. 1), instead of the belt members 102 and 104 being folded inward as in the embodiment shown. In alternative embodiments, the location and shape of the various hook and loop elements may vary. In still other embodiments, the one or more belt members may be permanently affixed to the spinal support element 114, via other components or directly.

Figure 11:
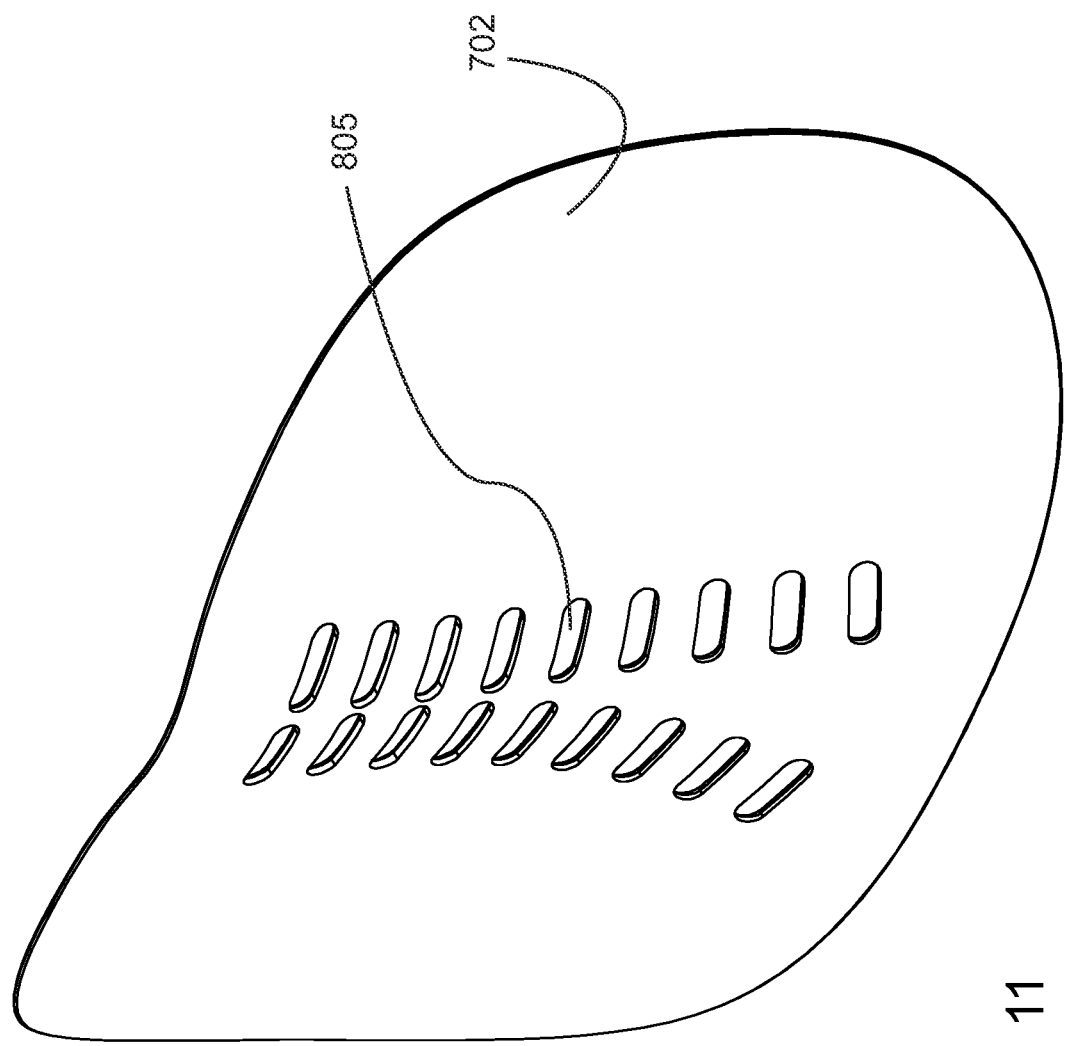
FIG. 11 shows a posterior perspective view of a foam pad used in the spinal support element in some embodiments.

FIG. 11 shows a posterior perspective view of foam pad 702 used in the spinal support element 114 in some embodiments. As described above, foam pad 702 may be made of a suitable material such as open cell foam or styrene foam for providing cushioning support to a user. Foam pad further provides breathable orifices 805 to further facilitate the flow of air in and out of the spinal support element structure 114 for patient comfort. In an embodiment, the orifices are die cut.

Figure 12:
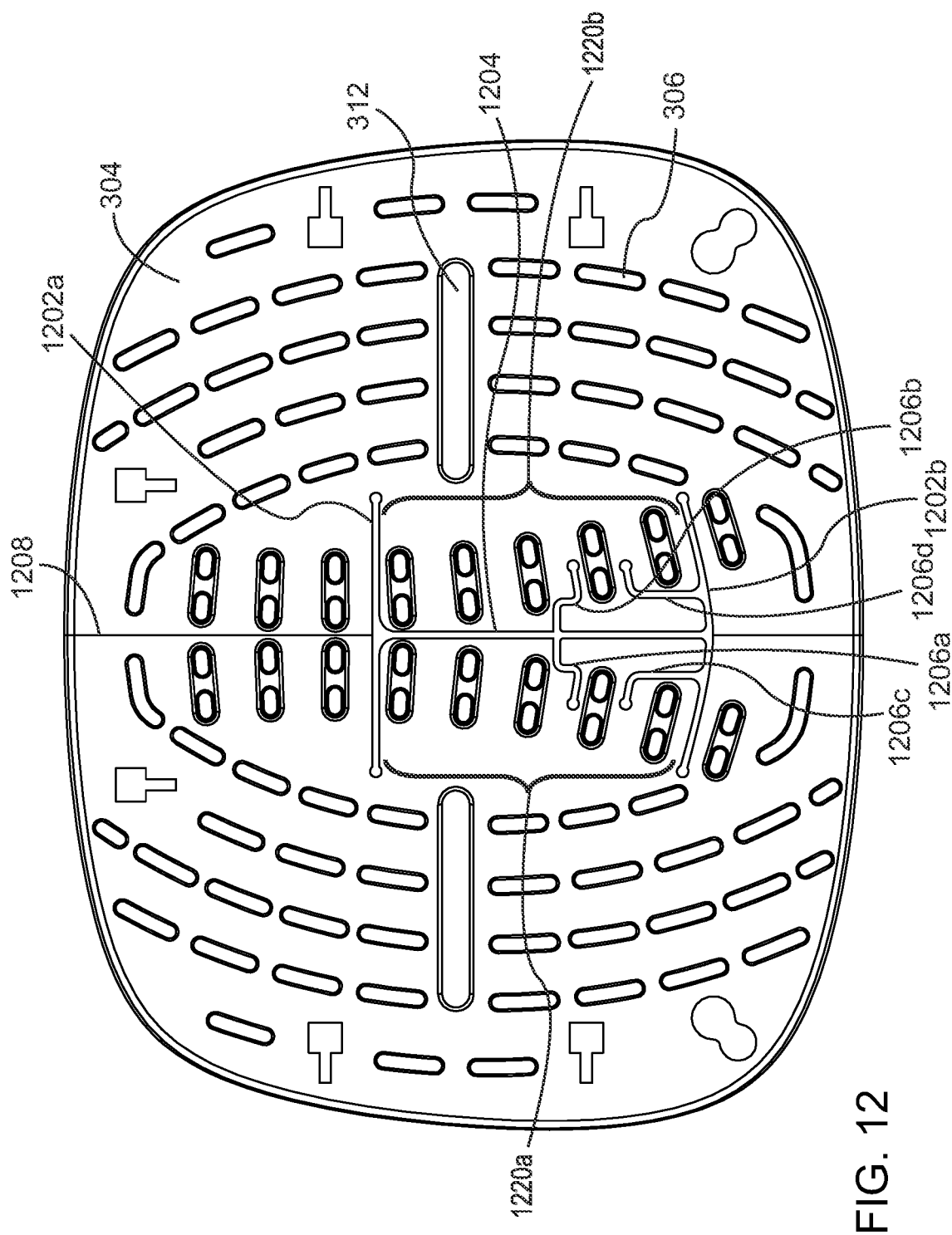
FIG. 12 shows a posterior front view of the posterior frame having a structure configured to minimize patient discomfort in accordance with an aspect of the disclosure.

FIG. 12 shows a posterior front view of posterior frame 304 having a structure configured to minimize patient discomfort in accordance with an aspect of the disclosure. As discussed in connection with previous embodiments, posterior frame 304 may be a generally semi-rigid structure used to provide the necessary support to the spinal column when the back brace is worn by a user. As noted previously, posterior frame 304 includes various capsule shaped orifices 306 for breathability and in some embodiments, for effecting the bendability or other design considerations relevant to the posterior frame 304 for maximum effectiveness. Further shown are orifices 312 to enable the posterior frame 304 to slidably connect to the D-rings 126a-b in accordance with an exemplary embodiment.

Oftentimes, the user of the back brace has just gone through surgery or otherwise has bruising, pain or other trauma to the affected area of the spine over which the orthopedic back brace is configured to operate. In conventional back braces, the rigid or semi-rigid portion of a spinal pad can serve to significantly exacerbate the pain of the user. This is particularly true where the user has surgical wounds or other trauma in the affected area. In these cases, conventional back braces, due to the rigidity in the area of the plastic spinal pad, tends to provide a significant amount of force and pressure to the affected area, tending to cause a user afflicted with such trauma considerable pain. As a result, the user is less motivated to wear the back brace.

Accordingly, in one aspect of the disclosure, a set of strategically-positioned perforations in posterior frame 304 enable a breathable and moveable "doorway" to partially open and provide relief to the user by avoiding excess or undue pressure on the injured area. As seen in FIG. 12, posterior frame 304 includes a generally central region positioned between line segment 1208 which is the area that is typically directly against the injured area. In FIG. 12, perforations 1202a and 1202b in the plastic material are provided and are connected together by another orthogonally-disposed perforation 1204. Additional perforations 1206a and 1206b run transversely through perforation 1204, and perforations 1206c and 1206d run orthogonally to perforation 1202b, such that a network of perforations is defined. This network ultimately defines a pair of flaps 1220a and 1220b. When the orthopedic back brace as described herein is donned by a user, the network of perforations, and particularly perforations 1202a-b and 1204, enables the flaps 1220a-b to partially open to thereby relieve pressure due to spinal processes (e.g., natural spinal movements) on the affected area of the user's spine. In this way, the orthopedic back brace of the present disclosure provides the necessary amount of compression and adjustment to the spinal region without causing further trauma or unnecessary pressure on the affected area of the user.

In the embodiment shown, perforations 1206a-d have been strategically placed to further allow a user to connect the posterior frame 304 of spinal support element to a single or double loop on a user's pant to prevent unwanted sliding or movement of the orthopedic back brace when the user sits or performs other movements. Additionally, perforations 1206c-d and a portion of perforation 1202b may produce another flap orthogonal to flaps 1220a-b, which flap may be used to clip onto an edge of a user's pant in lieu of using a belt loop connection.

In addition, in some embodiments, perforations 1206a-d, or positional variations of such perforations, may be configured to provide additional degrees of freedom or orientations such that the flap sections 1220a and 1220b (and segments within the flap sections 1220a and 1220b) can move in slightly different orientations to further relieve undue compression in an injured spinal area while maintaining an effective overall compression to straighten the spine.

In short, flaps 1220a-b can be made to provide comfort and support and pressure relief in the most delicate area of the user's spine, and this support can be provided, in one embodiment, by enabling the network of perforations to allow the segments and flaps 1220a-b to partially open. Advantageously, such flaps also provide a mild pressure gradient rather than a sharp change in compression as in conventional approaches. In particular, conventional attempts to address this problem include the use of small "windows" or holes in the frame of a back brace. Unlike the flexible flap structure as described in the present disclosure, these conventional window mechanisms tend to compress against the user's back and cause the user to experience "window edema" in which substantial pain and swelling within the confines of the window area may occur. Also, these conventional windows intrinsically include sharp demarcation lines defined by the window perimeter, which lines can result in abrupt and painful pressure differences on the affected area.

The above-described flap solution, by contrast, provides gradient support and relief, and substantially eliminates the deficiencies caused by sharp edges per conventional solutions. The gradient support as described above also reduces pressure on the affected area significantly, including when the user is sitting, while concurrently maintaining the structure of the posterior frame 304.

It will be appreciated that, while a specific network of perforations is described herein to effect the desired objectives, the principles of the present invention can be practiced using different configurations, and different networks or types of perforations. That is, the segments 1220*a* and 1220*b* and the associated network of perforations is illustrative in nature, and any number and shape of perforations, flaps, etc., can be further designed to accommodate the sensitive areas of the patient's spinal region without departing from the spirit and scope of the teachings herein.

Figure 13:
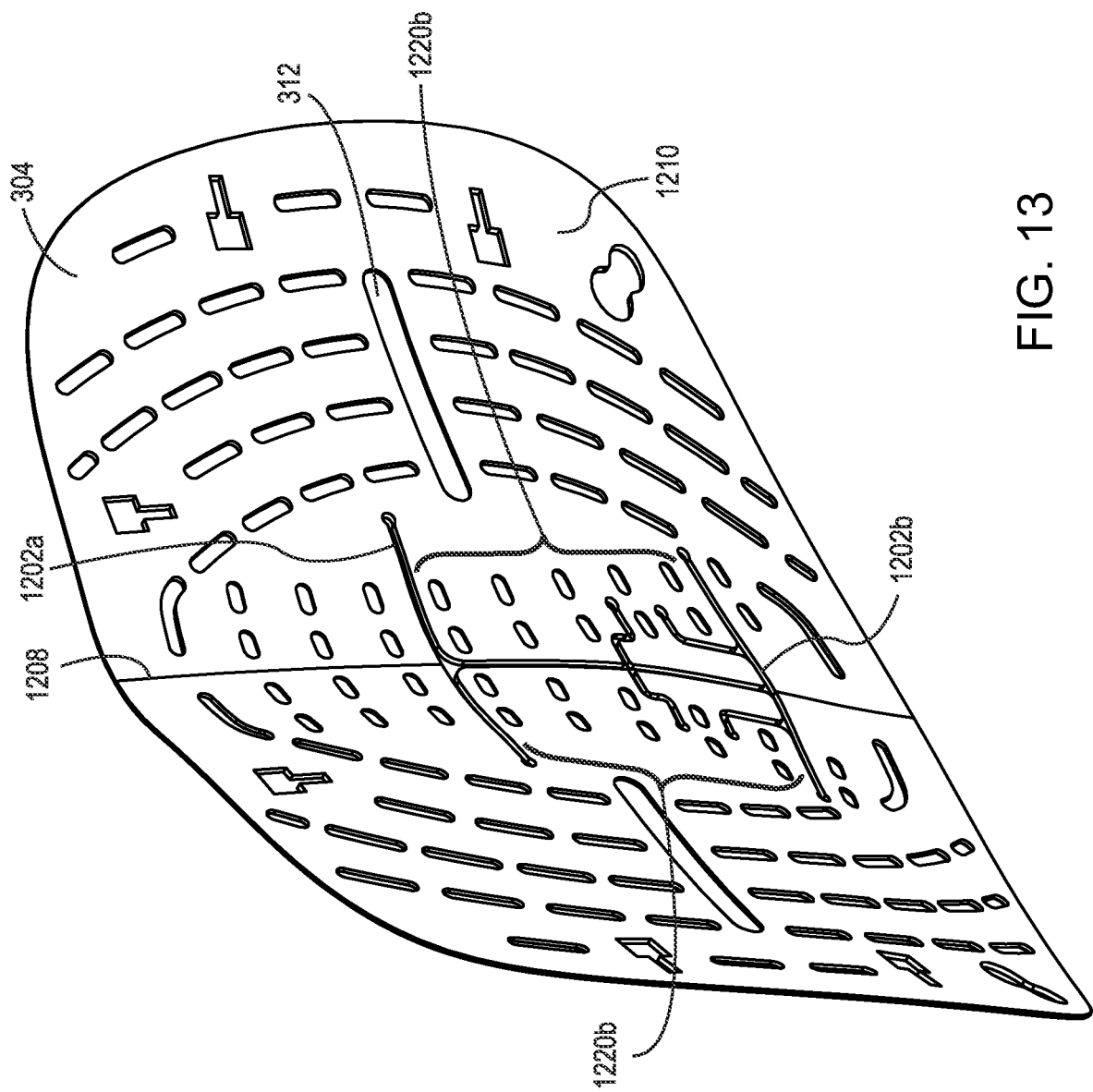
FIG. 13 shows an anterior perspective view of the posterior frame having the structure configured to minimize patient discomfort.

FIG. 13 shows an anterior perspective view of the posterior frame having the structure configured to minimize patient discomfort. The anterior side 1210 of posterior frame 304 is slightly angled outwardly about an axis defined by line 1208. Thus, when the posterior frame 304 is compressed against a user's spine as the user dons and properly fits the back brace, the overall structure of posterior frame 304 provides the compression and spinal support needed for the user while the network of perforations located in an affected area of the user can extend outwardly to relieve pain and uncomfortable pressure on the user's spine, including on a recent surgical scar or an injury.

In another aspect of the disclosure, a compact and low-profile orthopedic back brace is disclosed which uses thermal fusion to integrate together the materials in the belt member. As noted above, conventional back braces use stitching as a primary means of assembling the belt members. As a result, conventional back braces are unduly large and bulky. As for the stitched belt members of the present art, the various layers are bulky and are generally independent of one another. Because they are independent, they tend to separate in some areas and congregate or "bunch up" in other areas. It is the experience of the inventors that users generally prefer smaller and more compact orthopedic devices, given, among other problems. the potential for particularly self-conscious people to avoid wearing the devices altogether.

In addition to their bulkiness and layer independence of the belt members, conventional back braces have other deficiencies. Oftentimes it is desirable to use materials in the belt member(s) having different properties or characteristics in order to achieve a particular objective. Such particular objectives may include, by way of example, a specific amount of rigidity in various areas of the belt member and a specific amount of elasticity in other areas of the belt member. Sometimes it is desirable to combine these characteristics and obtain specific degrees of rigidity, stiffness, elasticity, or specific gradients of such characteristics across the area of the belt members. Conventional back braces endeavor to obtain these objectives by stitching disparate materials together.

For example, such conventional back braces may have belt members with regions in which two versions of a given material—one thick and the other thinner—are stitched together. Additionally, such conventional back braces may have belt members with different types of materials stitched together to achieve the aforementioned objectives. A significant disadvantage to this process is that where materials having different characteristics are stitched together at some border region along a surface of the belt member, that border region will generally be characterized by a sharp and abrupt discontinuity in the physical characteristics and properties of the belt member along that border region. For example, a conventional back brace may use a belt member having a thick, relatively inelastic material that in turn is sewn to a relatively elastic material. The properties at the stitched region change dramatically from inelastic to elastic—a change that may result in uncomfortable pressure points or other anomalies, and one is more often than not noticeable to the user of such conventional back braces.

In contrast to conventional back braces, a more compact and lower-profile orthopedic back brace includes materials welded together, at least in part, by thermal fusion. Generally, welding is a process where two or more pieces of materials such as thermoplastics, foam, mesh, etc., are fused together by use of heat, pressure and the passage of time. The process of applying heat softens the material and enables it to affix or fuse to another material when an adequate amount of pressure is applied. A filler material may be used in some thermal fusion processes, such as the use of an adhesive to join two materials that have properties that are not necessarily amenable to the welding process without the filler material.

Different types of welding are available and any suitable welding technique may be contemplated herein. Additionally, different types of weldable materials are available, each with different melting temperatures or bonding properties. These and other variables dictate various factors like whether two different materials can be thermally fused together directly, or whether an additional filler material is desirable.

Some examples of welding methods include heat press, RF welding, sonic welding, and a number of forms of high frequency welding. Depending on materials and bonding methods, different bonding and melting temperatures of the materials are involved in the typical welding process. In general, the temperature range is 90 C-250 C, but this range may not be applicable to all such processes, and some temperatures may be higher or lower than the aforesaid range. Radio frequency (RF), sonic and most forms of high frequency welding create heat by vibrating materials against each other. This phenomenon enables the materials to create their own heat energy, which in turn fuses the materials. Other methods of thermal fusion may include use of a heat press, whereby application of high temperature to the layers thermally fuses them. In one embodiment, high frequency welding is used to create the orthopedic back brace described in the present disclosure.

In contrast to the conventional back braces described above, the thermal fusion process heats the materials and with added pressure, causes the materials to fuse as a substantially integrated unit around the fusion areas. Thus, at the region of thermal fusion, the resulting integrated material typically possesses collective characteristics or properties of each of the constituent original materials. As a result, at regions where the materials are fused together, a gradual gradient or change in material characteristics (e.g., rigidity, elasticity, stiffness, etc.) can be designed and implemented in the belt member. As a result, when a user wears the orthopedic back brace as described wherein, the user is much less likely to notice abrupt discontinuities resulting from these phenomena. This effect is due in part to the fact that the thermal fusion process integrates the materials together to form a unitary segment rather than a set of independent layers of materials as seen in conventional techniques. Where welding is used on the fabrics and materials, the gradients in properties can be designed to be very gradual.

Moreover, because the thermal fusion process typically involves applying significant pressure to the material, the materials involved in the process are generally compactified. That is, they are made smaller by virtue of being integrated together at the fusion regions. As a result, the orthopedic back brace as disclosed herein can advantageously be made significantly smaller and more compact than conventional devices. Because the back brace as disclosed herein is less bulky and unwieldy, it is more comfortable to wear than conventional devices. Moreover, the thermal fusion process need not be applied at a defined border region, unlike in stitching processes. Rather, the thermal fusion process may be applied across a substantial region of the overall materials. As a result, the resulting unitary segment may substantially less voluminous and may be seamlessly fused together with properties having values spread gradually across the segment. In short, unlike conventional techniques that use stitched belts with independently acting layers, the belt members of the back brace disclosed herein may in some embodiments form a unitary segment that can essentially act as a single integrated material.

FIG. 14A discloses a front posterior view of the belt member 104. As described above, belt member 104 includes winged member 116b which in one embodiment includes UBL material. Further included are exterior layers 119b, belt end segments 108, and UBL region 112. FIG. 14B discloses a front anterior view of the belt member 104. The anterior portion includes winged members 220b, hook sections 906a (used in one embodiment for securing the belt member 104 to D-ring 126b via a hook and loop connection with winged members 220b), belt end segment 208 and connection portion 210. In an embodiment, each of these materials of belt member 104 are welded together using thermal fusion to form a unitary segment acting as a single structure and having continuous properties as described above.

Figure 15:
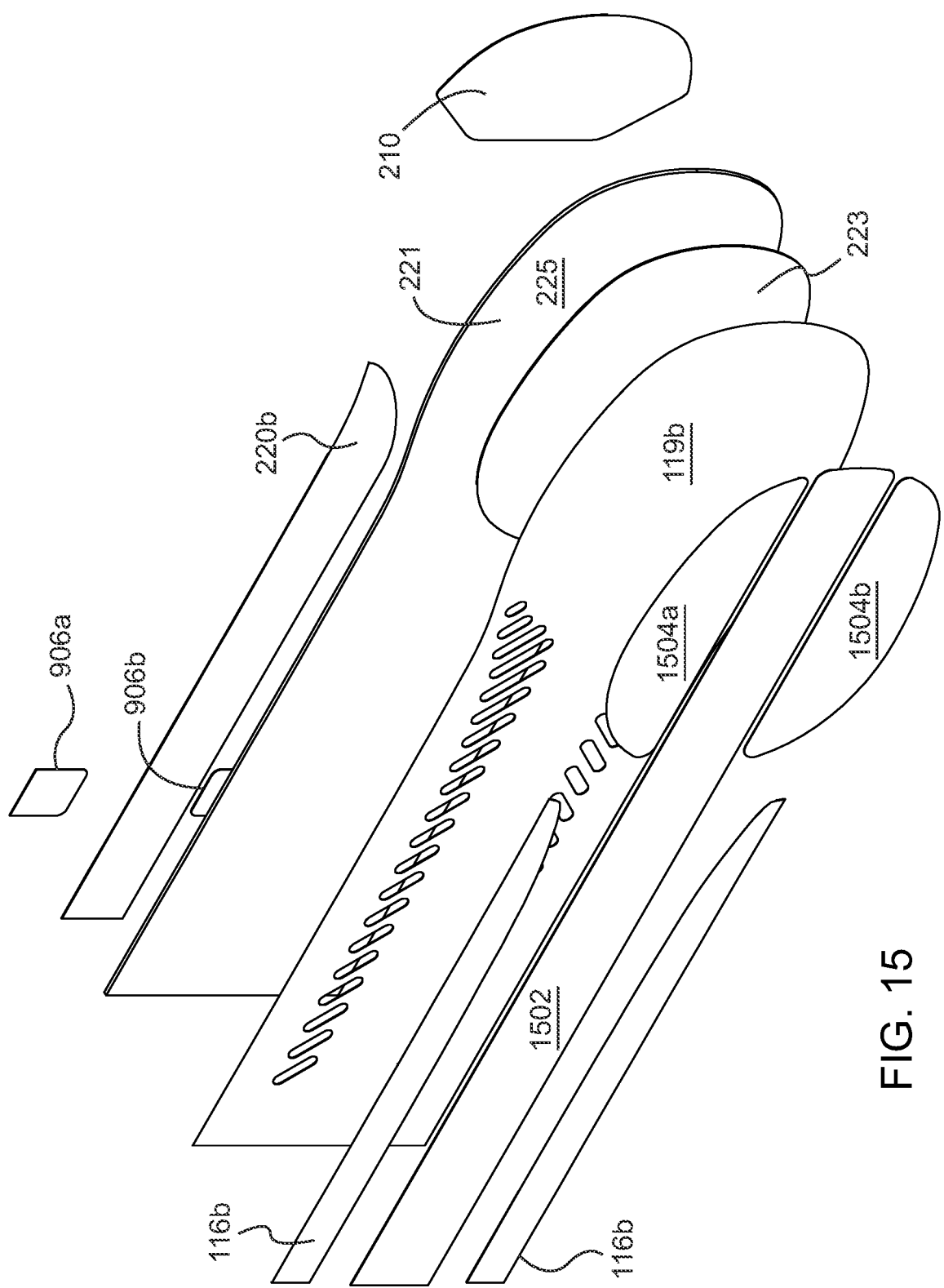
FIG. 15 shows a staggered perspective view of a belt member having its components disassembled into their constituent parts.

FIG. 15 shows a perspective view of belt member 104 having its components disassembled into their constituent parts. These include winged members 116b, exterior layer 119b, anterior portion 221, winged members 220b, connection portion 210, glue portion 223, and hook regions 906a-b. In the embodiment shown, winged members 116b and 220b are composed of UBL and are made to be substantially rigid to enable a better fit against the waist and front torso of the user. This rigidity can, in one example, be gradually provided to winged members 116b and 220b by thermally fusing winged members 116b to exterior layer 119b and by thermally fusing winged members 220b to anterior portion 210. In an exemplary embodiment, exterior layer 119b is composed of TPU. TPU has several advantages when used in a thermal fusion process. For one, TPU can fuse with other materials, such as hook and loop materials, directly without the use of a filler material. During the thermal fusion of UBL winged members 116b to exterior TPU layer 119b, the TPU can act as an adhesive and can melt to integrate with the UBL in winged member 116b. In addition to its ability to act as an adhesive, TPU is a versatile material that can be made to be elastic or inelastic depending on its thickness. Consequently, where more stretch is desired on a belt member, TPU can be limited or it can be made thinner. In addition, thermal fusion in general, and particularly thermal fusion of TPU with UBL, causes compression of the integrated materials. This compression is highly advantageous as it enables the belt to be made smaller, as previously described.

Referring still to FIG. 15, exterior layer 119b may be thermally fused to anterior portion 221. In an embodiment, anterior portion 221 is composed of 3-D spacer mesh. Here again, the TPU of exterior layer 119b seamlessly fuses with the 3-D spacer mesh of anterior portion 221, compressing the materials further. While in some embodiments the exterior layer 119b is directly fused to anterior portion 221, in other embodiments a thin adhesive film may be placed between exterior layer 119b and anterior portion 221 to enable greater control over the bonding process for more consistent bonding.

In a further exemplary embodiment, a hot melt glue board or polycarbonate section 223 is applied between exterior layer 119b and anterior portion 221 at an end section 225 of the anterior portion 221 and exterior layer 119b. Because the glue board is rigid at room temperature and hardens further during the thermal fusion process, further rigidity to the end section 225 of anterior portion 221 can be provided for a more controlled and comfortable fit. It should be noted that end section 225 may generally correspond to the area of one of belt end segments 106 and 108 (FIG. 1). This area corresponds to a front stomach area of the user, wherein some stiffness is beneficial for comfort and for ensuring a secure fit, thereby enabling the back brace to properly function. In an exemplary embodiment, the section 223 is only applied at one of belt segments 106 or 108. Other configurations may not utilize section 223.

In addition, connection portion 210 may be thermally fused to an anterior side of anterior portion 221. Winged members 220b may be welded to the anterior side of anterior portion 221 in like manner. In turn, square hook sections 906a and 906b may be welded over the winged member 220b. In an embodiment, winged member 220b is composed of UBL.

FIG. 15 further shows UBL segment 1502 and belt end segments 1504a-b, also composed of UBL in the present embodiment. UBL segment 1502 and belt end segments 1504a-b are thermally fused to exterior layer 119b.

The amount of materials used, such as the thickness of the TPU and 3-D spacer mesh, can be controlled to achieve certain target properties within the belt. The use of an adhesive during thermal fusion can be beneficial in some situations. For example, the adhesive has a low melting point such that during welding, the adhesive may melt first and fuse to two other materials that otherwise have higher melting points.

Referring back to FIG. 1, in some embodiments a binding or piping process may be applied along the tangent edge 151 of belt members 102 and 104 to secure the edges of the belt members 102 and 104.

The use of welding as described herein has several additional advantages. Because most or all of the materials of the belt assembly are fused together, the welded belt assembly may be made waterproof. Further, the welded belt assembly may be contoured. While conventional stitching and lamination techniques typically result in flat belt assemblies characterized by essentially two-dimensional features not naturally aligned with the dimensions of the user's anatomy, thermal fusion can be used in accordance with an embodiment to contour the belt to an effectively three-dimensional shape. More specifically, in this embodiment, thermal fusion can be used to shape the belt to conform to the anatomy of a user. This capability may provide a significant additional benefit of comfort to a user. Moreover, such welding processes can be employed to provide a variety of different shapes and customized contours that are configured to fit securely and comfortably given a particular user's size and anatomy.

Figure 17A:
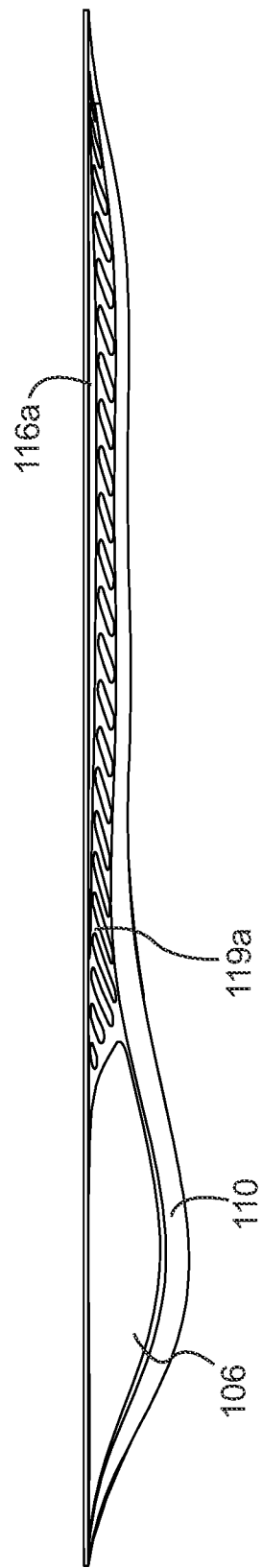
FIG. 17A shows an inverted side view of the belt member of FIG. 16A.
Figure 17B:
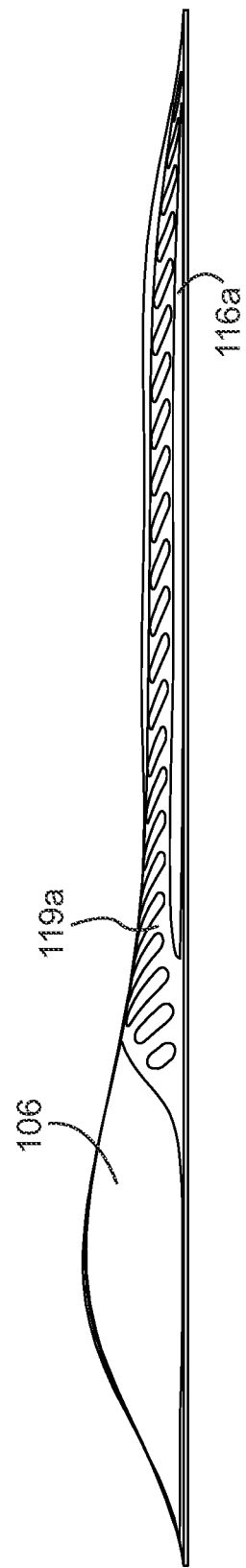
FIG. 17B shows a side view of the belt member of FIG. 16A.
Figure 18B:
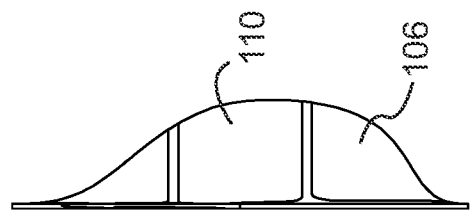
FIG. 18B shows a vertical side view of the belt member of FIG. 16A as viewed from a proximal end section of the belt to the distal belt an segment.
Figure 18A:
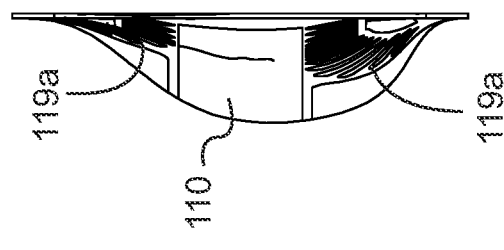
FIG. 18A shows a vertical side view of the belt end segment of the belt member of FIG. 16A.

FIG. 16A is a front posterior view of belt member 102, including exterior layers 119a, belt end segment 106 and region 110. FIG. 16A further defines cross sections A-A and B-B of belt 102. FIG. 16B shows a cross-sectional view of belt member 102 along plane A-A. The view along plane A-A coincides in this embodiment with belt end segment 106 and region 110. Because the belt layers are welded together, the belt member 102 can be gradually contoured (1604). While the magnitude of the contour may be exaggerated for illustration purposes in FIG. 16B, this contour can be specifically designed to accommodate the anatomy of a user or class of users and can be customized to meet the needs of users with different body shapes. FIG. 16C shows a cross-sectional view of belt member 102 along plane B-B. Plane B-B corresponds to a central area of belt member 102 and, as in the previous illustration, this region can be similarly contoured in an appropriate manner to conform to a user's anatomy for a secure and comfortable fit. Conventional back braces lack this feature. In conventional braces, the otherwise flat belt must be secured to the curved shape of a user's anatomy by tightening the belt sufficiently to enable the back brace to properly function. This tightening may result in additional pressure points and discomfort, particularly after the conventional brace is worn for long periods of time. FIG. 16D shows a perspective view of the belt member of FIG. 16A. FIG. 17A shows an inverted side view of the belt member 102, including belt end segment 106, region 110, exterior layer 119a, and winged section 116a. FIG. 17B shows a side view of the belt member 102. FIG. 18A shows a vertical side view as seen toward the belt end segment 106. FIG. 18B shows a vertical side view of the belt member of FIG. 16A as viewed from a proximal end section of the belt to the distal belt an segment. In each of these views, the contour may not be drawn to scale and/or may be enhanced for clarity.

Figure 19A:
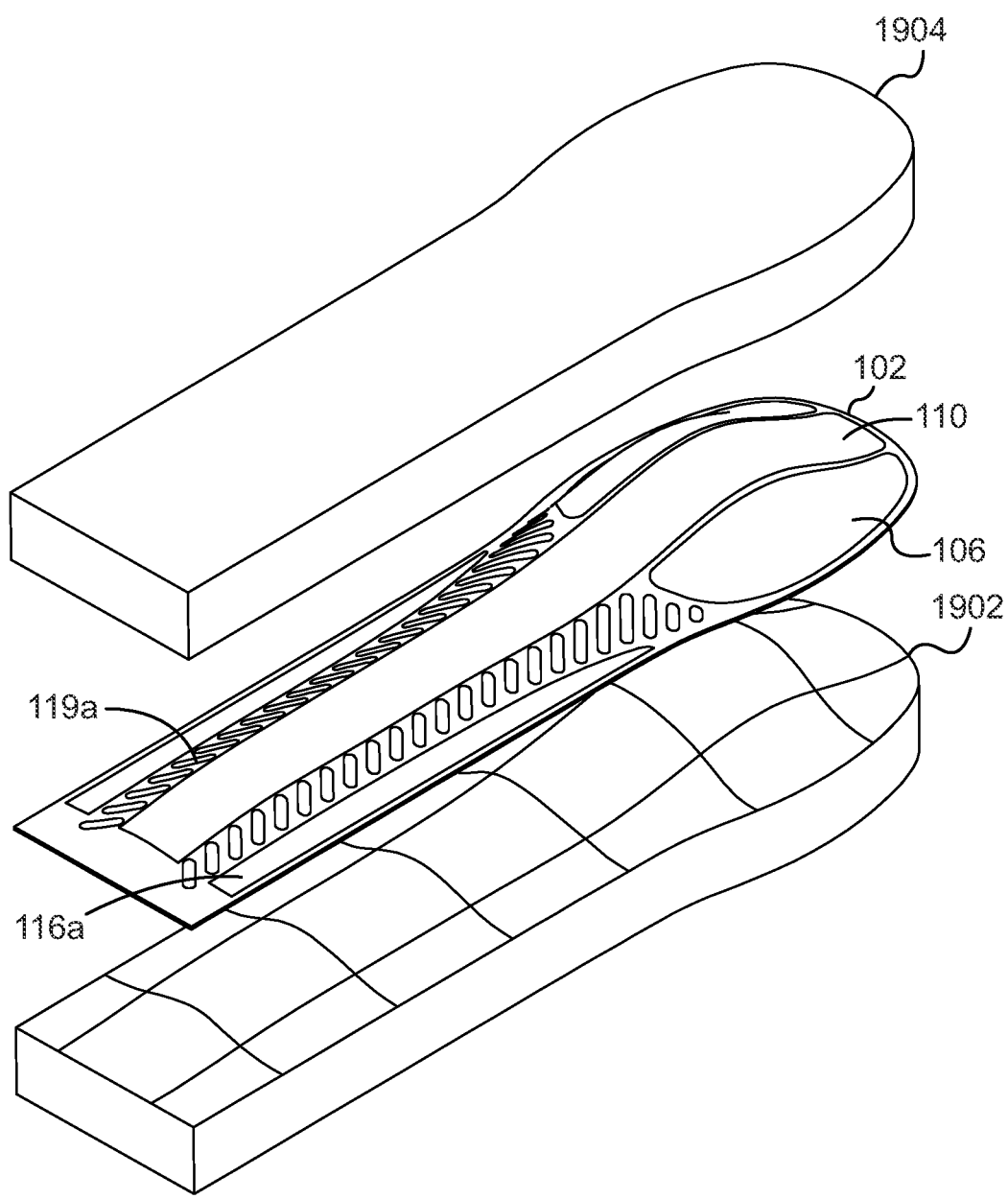
FIG. 19A shows a perspective view of a belt assembly disposed between two tooling molds for use in thermally fusing the belt assembly.

FIG. 19A shows a perspective view of a belt assembly disposed between two tooling molds for use in thermally fusing the belt assembly. This figure illustrates a technique for thermally fusing the belt assembly. Belt member 102 is shaped in this example using tooling core mold 1902, which may form a positive side of a mold, and complementary tooling cavity mold 1904, which may form a negative side of the mold. The tooling molds 1902 and 1904 may be machined or otherwise constructed to include the desired three-dimensional contour as described above, if a contour is desired. In one embodiment, the tooling molds 1902 and 1904 are composed of a metal alloy, such as an aluminum alloy, or another material conducive to transporting heat for use in the fusion process. The various belt layers (see, e.g., FIG. 15) may initially be assembled on top of one another on tooling mold 1902. In an exemplary embodiment, a plurality of pins (not shown) may extend around a perimeter of tooling mold 1902 and may be used to temporarily secure the yet unbonded belt materials prior to welding. In other embodiments, other temporary fastening mechanisms may be used. (In the illustration, belt assembly is seen after welding as a pre-molded belt member 102 having a contour for clarity). Thereupon, the tooling mold 1904, designed with a contour that complements that of tooling shell 1902 fits over tooling mold 1904 and heat and pressure are applied over time to thereby fuse the materials together and create an integrated structure which may be contoured.

Figure 19B:
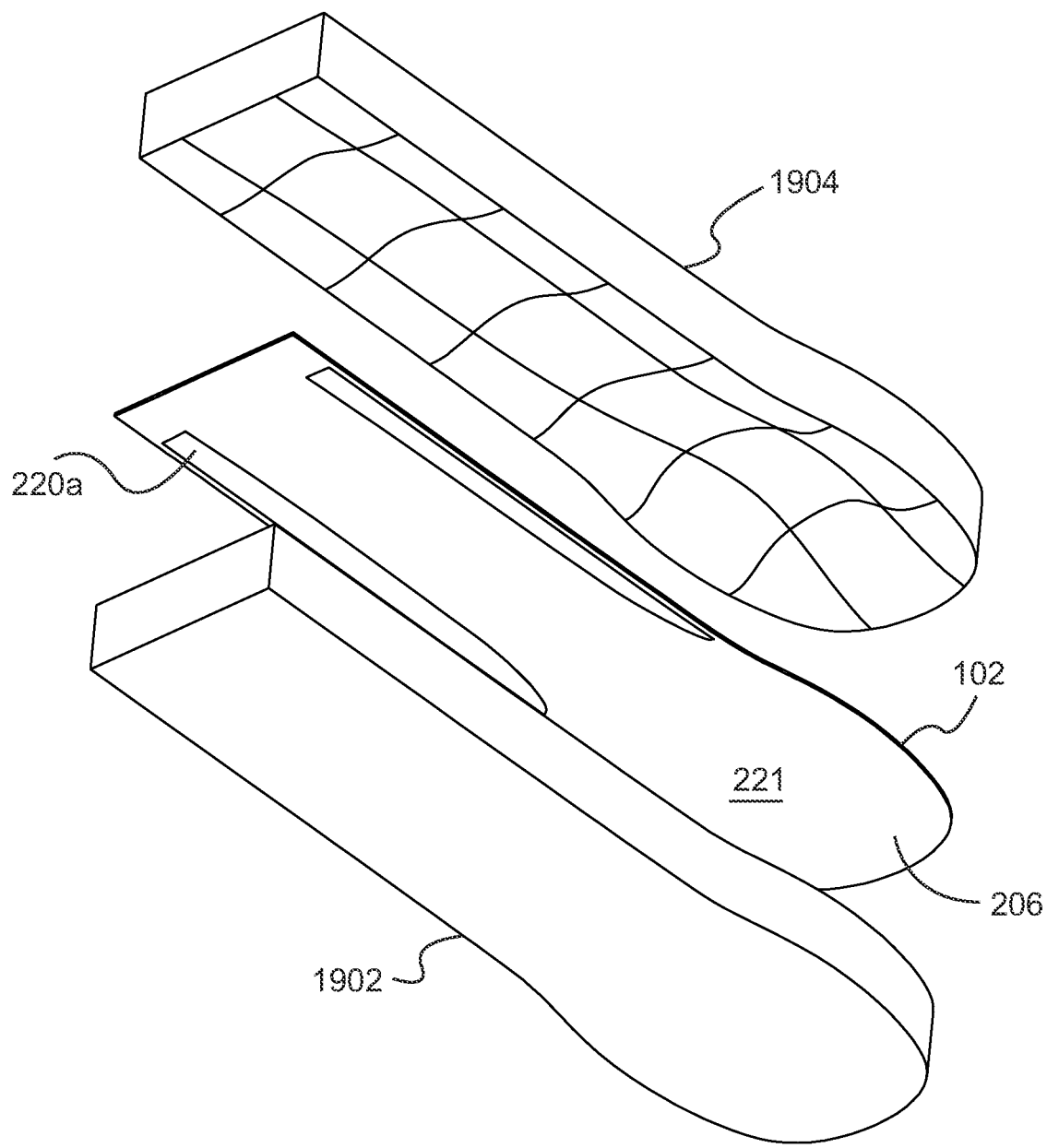
FIG. 19B shows an inverted perspective view of the belt assembly and tooling molds of FIG. 19A

FIG. 19B shows an inverted perspective view of the belt assembly and tooling molds of FIG. 19A. As shown in the illustration, tooling mold 1904 in this example in inwardly contoured in a desired shape to accommodate the belt assembly and tooling mold 1902.

Advantageously, whereas conventional techniques often require multiple stitching and/or gluing steps to form the resulting belt assembly and spinal support element, the welding process as described with respect to FIGS. 19A-B, above, can often be performed in a single step. For example, the material can be fused and contoured concurrently by using the above-described tooling molds.

It will be appreciated that alternatively or additionally, portions of the spinal support element 114 may also be contoured to form a three-dimensional shape. For example, posterior pad 202 (FIG. 2) may be thermally fused and contoured, whether by itself or along with other portions of spinal support element 114.

As described above, one benefit of the welding techniques is that properties of the belt member 102 itself, and specific regions of the belt, can be more carefully and strategically controlled than with conventional techniques. As an illustration, belt member 102 may include an exterior layer 119a composed of TPU (FIG. 1) fused with an anterior portion 221 composed of 3-D spacer mesh. The fusing of the TPU with the spacer mesh can substantially increase the strength of the fused TPU and spacer mesh as compared with the spacer mesh alone. In addition, the thermal fusion process is flexible. For example, hot melt glue (such as portion 223 in FIG. 15) can be inserted in the belt assembly being fabricated fused at an end segment 206 or 208 one of belt members 102 or 104 (or both) to increase the rigidity of the front section of the belt as worn by a user. This process can be contemporaneous with the belt assembly, as described above.

To demonstrate and verify the effectiveness of the thermal process versus conventional techniques, the inventors compiled test data regarding the relative stretching of various materials. The test data can be summarized as follows:

TABLE 1

Stretch Test

| Material Description | Process | Stretch Test (mm) - Initial Distance without Load | Stretch Test (mm) - Distance with 10 pound load after 2 minutes | Percent Change from Initial to Final Distance (%) |
| --- | --- | --- | --- | --- |
| Spacer Only | — | 205 | 245 | 19.51 |
| TPU Only | — | 203 | 225 | 10.84 |
| Spacer and TPU | Longitudinal Stitch | 200 | 222 | 11.00 |
| Spacer and TPU | Vertical Stitch | 200 | 223 | 11.5 |
| Spacer and TPU | Welded | 200 | 204 | 2.00 |

Summarizing the data in the above table, the inventors provided the listed materials and subjected them to a stretch test. The stretch test measured an initial distance of the material(s) without the presence of a stretching load, and a final distance of the material(s) upon application of a 10 pound stretching force. When 3-D spacer mesh was used alone as a benchmark, it was noted that the spacer buckled and necked substantially and elongated 19.51% as a result of the stretch. The TPU stretch test yielded an elongation of 10.84%. a little greater than ½ that of the spacer material. The stretch of the TPU also showed signs of bucking and necking of the material.

Next, segments of spacer mesh and TPU material were combined using vertical stitching. That is when viewing the material as a rectangle having a height substantially less than its base, the stitching was disposed vertically across adjacent left and right edges of the rectangle. The combined material was then stretched in the longitudinal direction (along the long axis of the rectangular material), resulting in an 11.5% elongation. It was apparent to the inventors that, even though the spacer mesh and TPU materials were stitched together, the TPU was sustaining the majority of the tension to hold the materials. It was concluded that the stitching of these materials does not create a generally stronger combination of the two materials.

Thereupon, the same spacer mesh and TPU material was used except that stitching was also applied longitudinally on each side of the combined segment. Thus, stitching traversed the perimeter of the material. The combined material was then stretched in the longitudinal direction, resulting in an 11.0% elongation, substantially similar to the case with only the vertical stitching. The same conclusions were reached as with respect to the vertical stitching case, and it was further concluded that the addition of longitudinal stitching does not create a generally stronger combination of the two materials.

Finally, the spacer mesh and TPU material were thermally fused pursuant to the principles described in the present disclosure. Subject to the stretch test, the combined materials elongated a mere 2% —more than five times less than either of the stitched cases. The welded combination is consequently substantially stronger than the combinations that rely only on stitching. The inventors further observed that the fused materials exhibited minimum buckling and necking. Thus, based on the observed data, the inventors have concluded that the thermally fused nature of the belt assembly as well as, in some embodiments, portions of the spinal support element, yield a stronger, more durable, longer lasting orthopedic back brace as compared to conventional structures.

Table 2 shows a compilation of data taken for various material combinations based on the application of the thermal fusion process. Specifically, Table 2 describes the average vertical pull of various material samples.

TABLE 2

Pull Test

| Material Name | Pull test Data (Kilogram-Force (kgf)) (Vertical Average) | Percent Change from Spacer (%) |
| --- | --- | --- |
| Spacer | 34.57 | NA |
| Spacer + TPU | 78.7 | 127.65 |
| Spacer + Hot Melt | 67.04 | 93.93 |
| Spacer + Hot Melt + TPU | 76.43 | 121.09 |
| Spacer + Hot Melt + TPU + UBL | 82.82 | 139.57 |

The data in Table 2 indicates, for example, that various characteristics (including strength) of the belt assembly may be achieved using different material combinations. In other embodiments, different welding parameters (e.g., temperature, pressure time of exposure) may be used to achieve different characteristics. In Table 2, the different material combinations may be used in different regions across the belt assembly to create gradual property gradients in the belt assembly. Further, the data reveals that the strength of the welded combination of spacer mesh and TPU material is more than twice that of spacer alone. Hot melt may be used for stiffness and rigidity in select portions of the belt assembly, but the data reveals that the strength is less than the spacer mesh/TPU weld. However, it is noteworthy from the data that adding hot melt to the spacer mesh/TPU combination assists in regaining that strength. The data also reveals that the welded combination of spacer, hot melt, TPU and UBL creates the strongest integrated material.

In short, using the principles described herein, the belt segment can be thermally fused to form a single integrated segment having well-controlled properties. The light weight, low volume nature of the resulting back brace will consequently be attractive to current users of large and bulky orthopedic devices, and new users of such devices.

While the belt segments of the orthopedic back brace have been described above as created substantially entirely using thermal fusion, it should be understood that this description is intended to be illustrative in nature and that stitching on the belt may also be used. For example, the use of sewing in one more parts of the belt members may be beneficial or cost effective in some instances such that some embodiments contemplate a belt that is partially integrated using thermal fusion and partially formed using conventional means such as stitching. These embodiments, which take advantage of the thermal fusion process to achieve all the benefits hereinbefore described, are within the scope of the present disclosure. It will also be appreciated that the materials described above are exemplary in nature, and new or different materials may be used or welded to form the belt assembly and/or the spinal support element. In addition, in some embodiments, portions or regions of the belt assembly and/or spinal support element may be composed of a single material. In still other embodiments, stitching and/or lamination may be used in combination with welding techniques, such as in other portions of the belt assembly or spinal support element, without departing from the spirit and scope of the present disclosure.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The various aspects of a flexible support presented throughout this disclosure are provided to enable one of ordinary skill in the art to practice the present invention. Various modifications to aspects presented throughout this disclosure will be readily apparent to those skilled in the art, and the concepts disclosed herein may be extended to other flexible supports. Thus, the claims are not intended to be limited to the various aspects of this disclosure, but are to be accorded the full scope consistent with the language of the claims. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An orthopedic back brace, comprising:
    a spinal support comprising a posterior frame, a posterior cover, and a posterior cover material comprising a mesh, said posterior frame, posterior cover, and posterior cover material fused together, and further comprising a posterior pad including a pad spacer section and a pad mesh element separated by respective strips of tape;

first and second belt members coupled to the spinal support via first and second D-rings, said D-rings cooperating with a pulley system, the first and second belt members comprising layers of unbroken loop (UBL) material sandwiching an intermediate layer, the layers of unbroken loop material and the intermediate layer fused together to form a unitary structure; and first and second pull rings affixable to the first and second belt members, the first and second pull rings coupled to the pulley system.

2. The orthopedic back brace of claim 1, wherein the intermediate layer is thermoplastic polyurethane.

3. The orthopedic back brace of claim 2, further comprising a polycarbonate material disposed between the intermediate layer and a layer of unbroken loop (UBL) material.

4. The orthopedic back brace of claim 3, wherein the polycarbonate material is hardened by fusing the first and second belt members.

5. The orthopedic back brace of claim 3, wherein the polycarbonate material is limited to a front of the orthopedic back brace configured to correspond to a user's stomach region.

6. The orthopedic back brace of claim 2, wherein a thickness of the thermoplastic polyurethane intermediate layer varies to yield different stretch characteristics on the first and second belt members.

7. The orthopedic back brace of claim 2, wherein the intermediate layer is directly fused to a layer of unbroken loop (UBL) material.

8. The orthopedic back brace of claim 2, wherein the intermediate layer is fused to a layer of unbroken loop (UBL) material using a thin adhesive film.

9. The orthopedic back brace of claim 2, further comprising a hook layer fused to a selected layer of said layers of unbroken loop (UBL) material at a surface opposite a surface fused to the intermediate layer, the hook layer configured to attach to a surface of unbroken loop (UBL) material.

10. The orthopedic back brace of claim 2, wherein the first and second belt members have a non-planar three-dimensional contour.

11. The orthopedic back brace of claim 1, wherein the posterior cover material is transparent.

* * * * *